United States Patent
Birdwell et al.

(10) Patent No.: US 6,741,983 B1
(45) Date of Patent: May 25, 2004

(54) METHOD OF INDEXED STORAGE AND RETRIEVAL OF MULTIDIMENSIONAL INFORMATION

(76) Inventors: John D. Birdwell, 15 Raintree Crossing, Oak Ridge, TN (US) 37830; Tse-Wei Wang, 15 Raintree Crossing, Oak Ridge, TN (US) 37830; Roger D. Horn, 705 Whirlaway Dr., Knoxville, TN (US) 37923; Puneet Yadav, 3400 Stevenson Blvd., Apt. B-38, Fremont, CA (US) 94538; David J. Icove, P.O. Box 1411, Knoxville, TN (US) 37901-1411

( * ) Notice: Subject to any disclaimer, the term of this patent is extended or adjusted under 35 U.S.C. 154(b) by 652 days.

(21) Appl. No.: 09/671,304

(22) Filed: Sep. 28, 2000

Related U.S. Application Data

(60) Provisional application No. 60/156,452, filed on Sep. 28, 1999.

(51) Int. Cl.⁷ .......................... G06F 17/30; G06F 7/00; G06F 17/00
(52) U.S. Cl. .......................... 707/5; 707/2; 707/104.1
(58) Field of Search ................ 707/5, 2, 10, 104.1, 707/101

(56) References Cited

U.S. PATENT DOCUMENTS

| | | | | |
|---|---|---|---|---|
| 5,325,466 A | * | 6/1994 | Kornacker | 706/61 |
| 5,442,562 A | * | 8/1995 | Hopkins et al. | 700/108 |
| 5,926,812 A | * | 7/1999 | Hilsenrath et al. | 707/5 |
| 6,026,397 A | * | 2/2000 | Sheppard | 707/5 |
| 6,100,901 A | * | 8/2000 | Mohda et al. | 345/440 |
| 6,122,628 A | * | 9/2000 | Castelli et al. | 707/5 |
| 6,490,582 B1 | * | 12/2002 | Fayyad et al. | 707/6 |

OTHER PUBLICATIONS

Juha Karhunen and Simona Malaroiu (1999), Locally Linear Independent component analysis, pp. 882–887.*

Cormen, Thomas H., Charles E. Leiserson, and Ronald L. Rivest, Introduction to Algorithms, MIT Press (Cambridge, MA) / McGraw–Hill (New York). 1990.

Guttman, A., R trees: a dynamic index structure for spatial searching, ACM, 1984, 47–57.

Sellis, T., et. al., The R*–tree: a dynamic index for multi–dimensional objects, Tech. Rept. UMI–ACS TR 87 3, CS TR 1975, University of Maryland, Feb. 1987, 1–24.

Agrawal, R. and J. C. Shafer, Method and system for performing proximity joins on high–dimensional data points in parallel, US Patent 5,884,320, Mar. 16, 1999.

Message Passing Interface Forum, MPI: A Message–Passing Interface Standard, version 1.1, Jun., 1995. Also at http://www–unix.mcs.anl.gov/mpi/and http://www.mpi–forum.org/docs/mpi–1 1–ht.

(List continued on next page.)

*Primary Examiner*—Safet Metjahic
*Assistant Examiner*—Merilyn Nguyen
(74) *Attorney, Agent, or Firm*—Banner & Witcoff, Ltd.

(57) ABSTRACT

A tree-structured index to multidimensional data is created using naturally occurring patterns and clusters within the data which permit efficient search and retrieval strategies in a database of DNA profiles. A search engine utilizes hierarchical decomposition of the database by identifying clusters of similar DNA profiles and maps to parallel computer architecture, allowing scale up past previously feasible limits. Key benefits of the new method are logarithmic scale up and parallelization. These benefits are achieved by identification and utilization of naturally occurring patterns and clusters within stored data. The patterns and clusters enable the stored data to be partitioned into subsets of roughly equal size. The method can be applied recursively, resulting in a database tree that is balanced, meaning that all paths or branches through the tree have roughly the same length. The method achieves high performance by exploiting the natural structure of the data in a manner that maintains balanced trees. Implementation of the method maps naturally to parallel computer architectures, allowing scale up to very large databases.

49 Claims, 29 Drawing Sheets-

OTHER PUBLICATIONS

Universal Data Option for Informix Dynamic Server, version 9.14 for Windows NT and UNIX. Also at http://www.informix.com/informix/techbriefs/udo/udo.pdf.

Geist, A., A. Begnelin, J. Dongarra, W. Jiang, R. Manchek, V. Sunderam, PVM: Parallel Virtual Machine: A Users'Guide and Tutorial for Networked Parallel Computing. MIT Press. 1994.

Beowulf Projects at CESDIR, http://cesdis1.gsfc.nasa.gov/linux/beowulf/, Center of Excellence in Space Data and Information Sciences, NASA Goddard Space Flight Center. 1998.

Strang, G., Linear Algebra and its Applications, 2nd ed., Academic Press, New York, 1980.

Budowle, Bruce and Tamyra R. Moretti, "Genotype profiles for six population groups at the 13 CODIS short tandem repeat core loci and other PCR based loci," Forensic Science Communications, FBI Laboratory Division Publication 99–06, U. S. Department of Justice, Federal Bureau of Investigation. Jul. 1999, V. 1, n. 2.

CODIS 5.1 GDIS Searching Specification (Draft), U.S. Department of Justice Federal Bureau of Investigation. Jul. 23, 1998.

Quinlan, J.R., Induction of decision trees, Machine Learning 1:81–106, 1986.

Berry, Michael W., Zlatko Drmac, and Elizabeth R. Jessup, "Matrices, vector spaces, and information retrieval," SIAM Review 41:335–362, 1999.

Hutson, William H., Method and System for Real–Time Information Analysis of Textual Material, US Patent 5,559,940, Sep. 24, 1996.

Hutson, William H., Method and System for Real–Time Information Analysis of Textual Material, US Patent 5,761,685, Jun. 2, 1998.

Castelli et al., Multidimensional Data Clustering and Dimensional Reduction for Indexing and Searching, US Patent 6,122,628, Sep. 19, 2000.

Castelli et al., Searching Multidimensional Indices using Associated Clustering and Dimension Reduction Information, US Patent 6,134,541, Oct. 17, 2000.

Message Passing Interface Forum, MPI–2: Extensions to the Message–Passing Interface, Jul. 18, 1997. Also at http://www.mpi–forum.org/docs/mpi–20–html/mpi2–report.html.

* cited by examiner

SINGLE HOST SEARCH SERVER d16s539 Divided into 6 Partitions

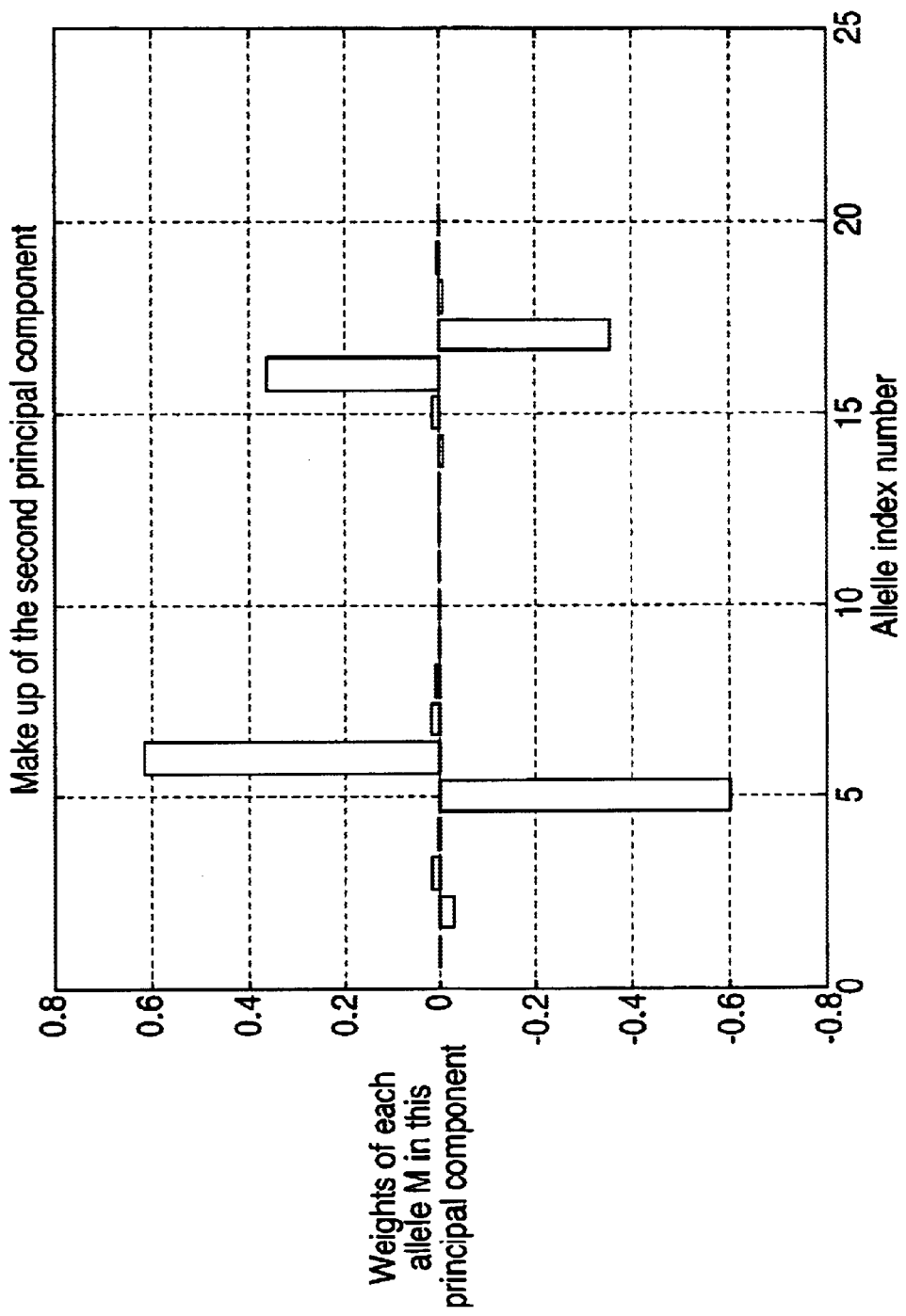

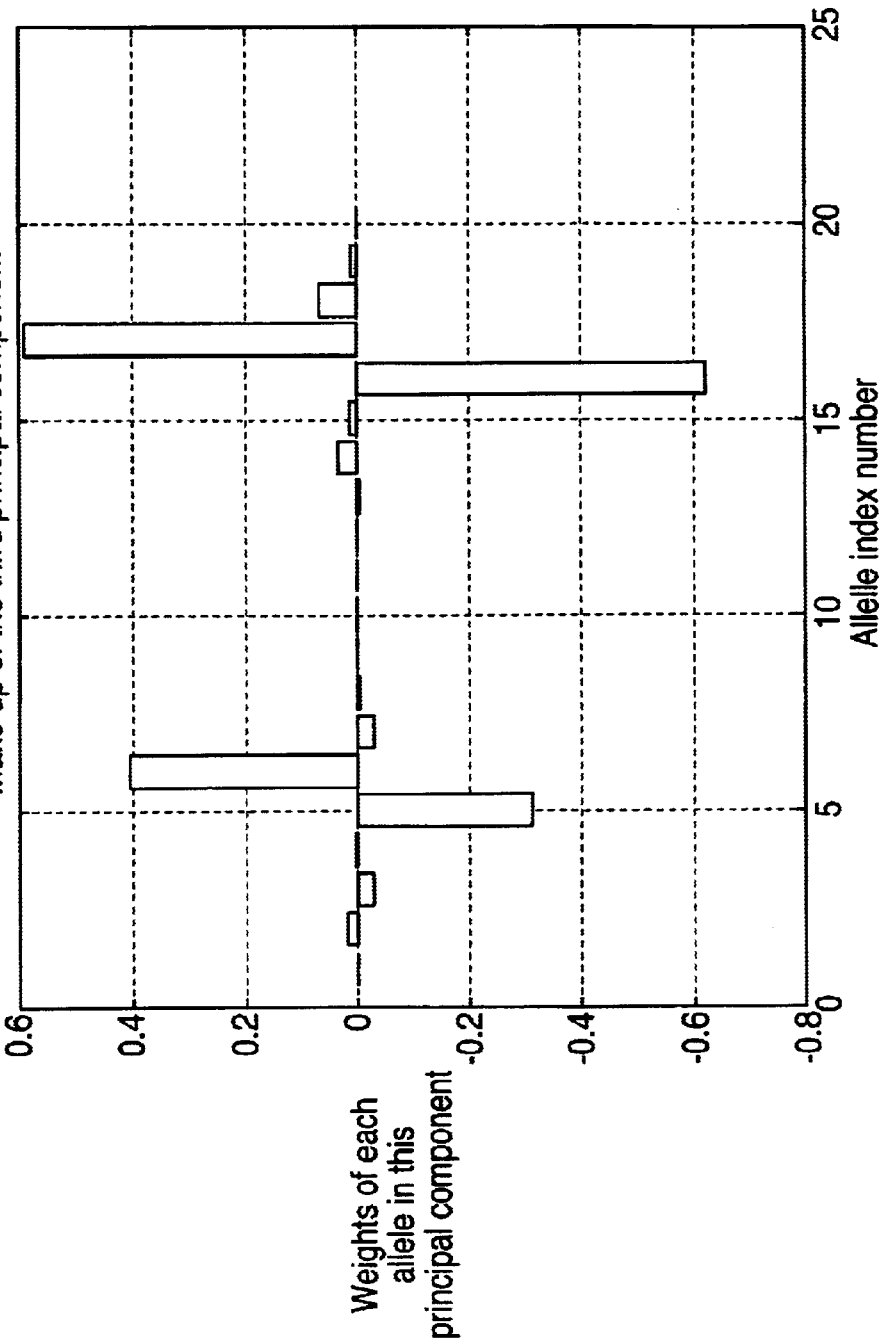

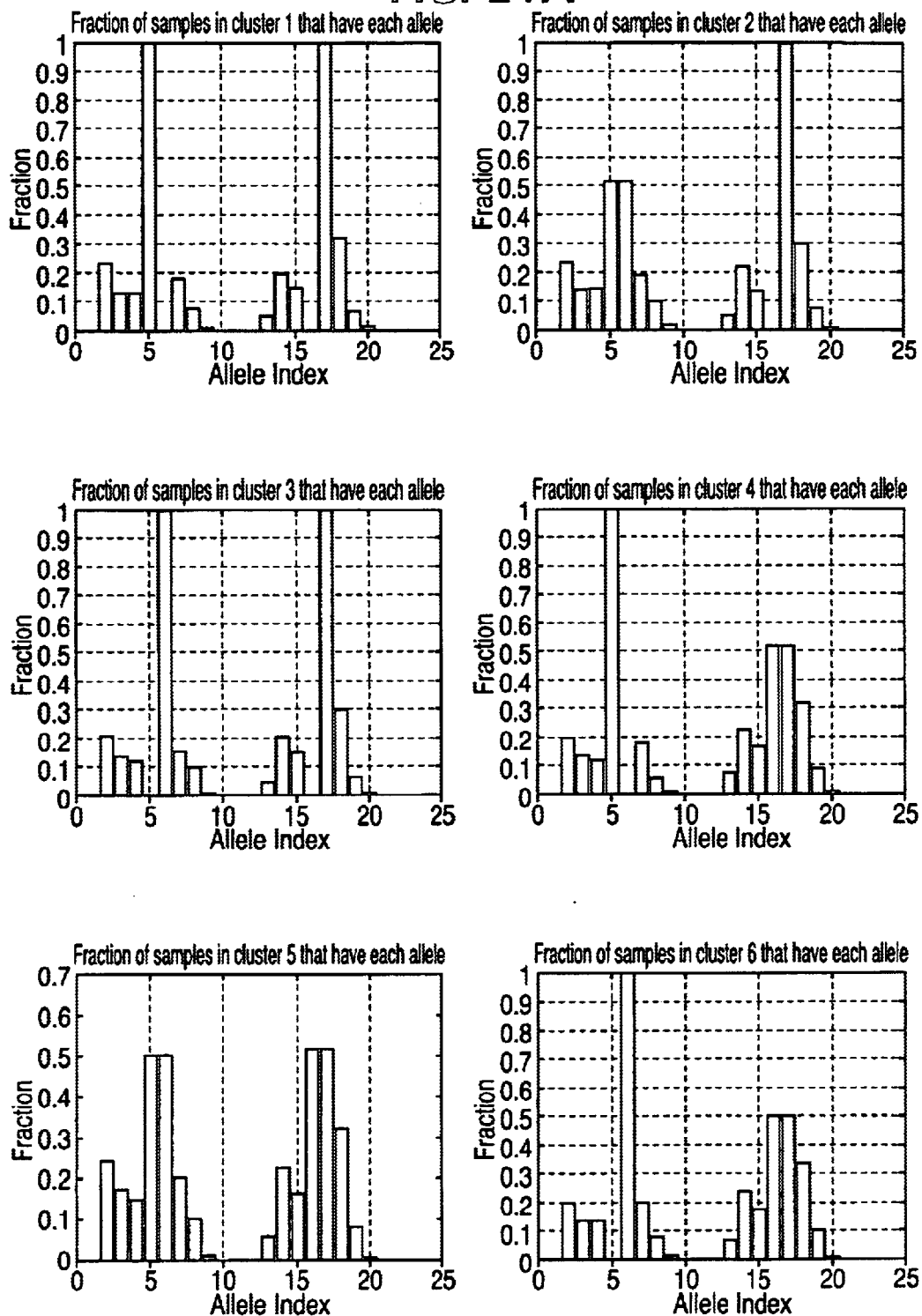

FIG. 21B
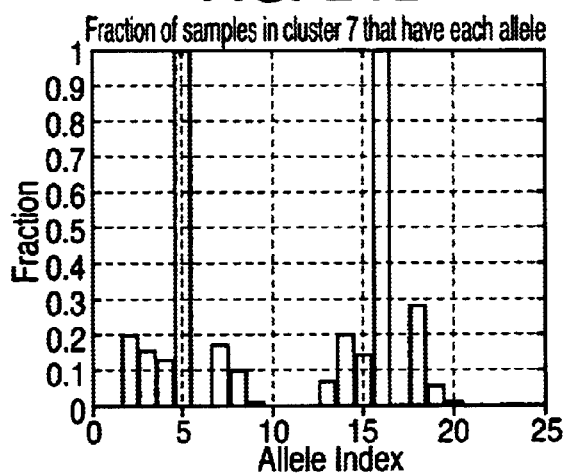
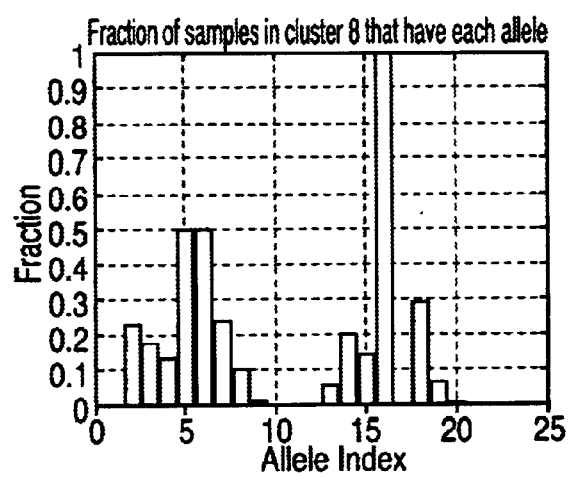
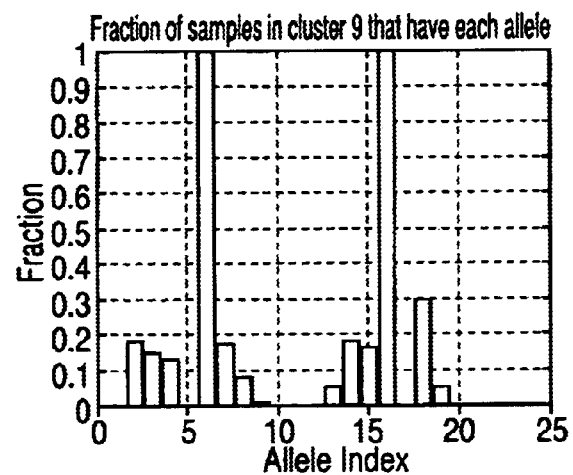

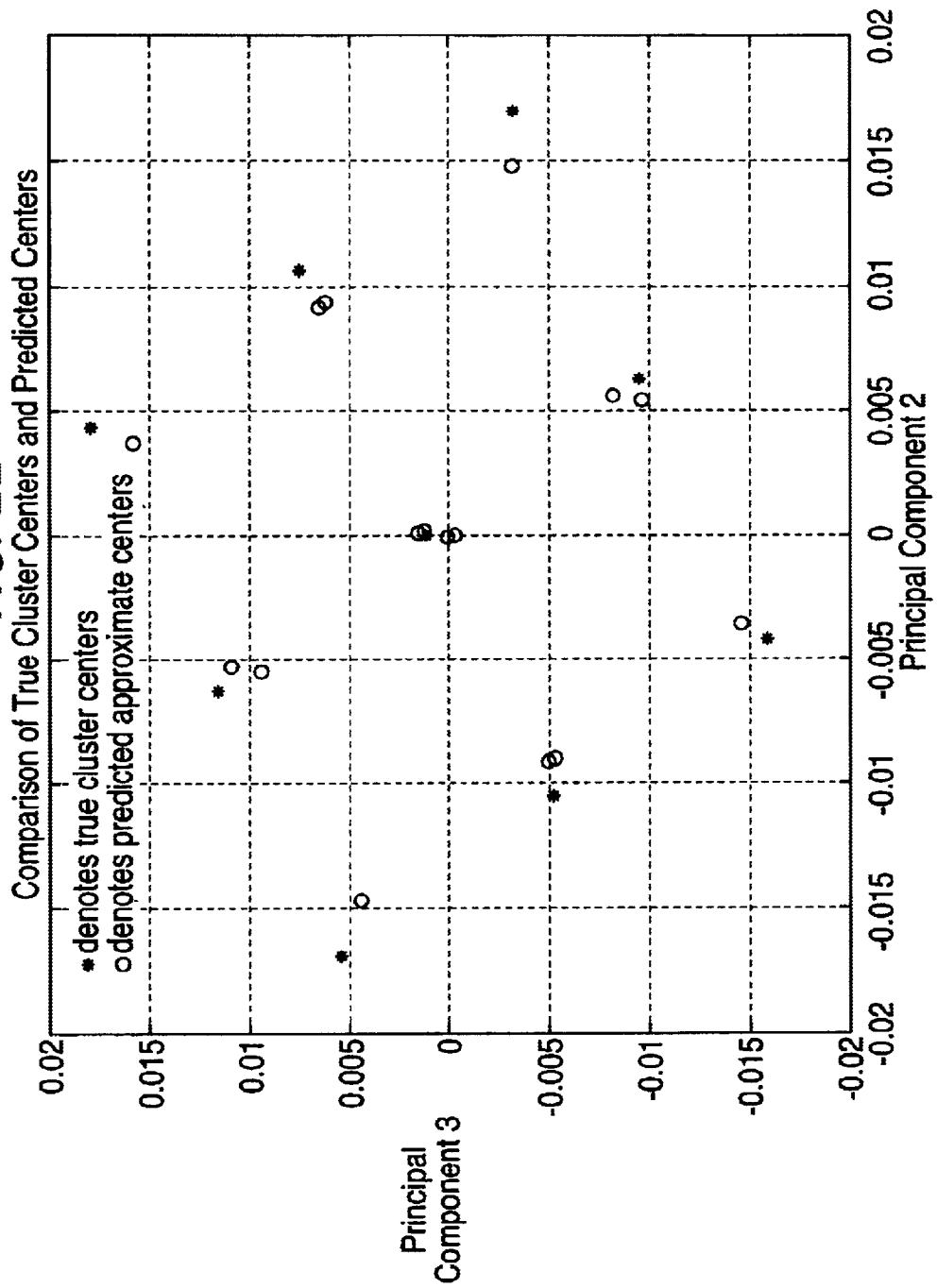

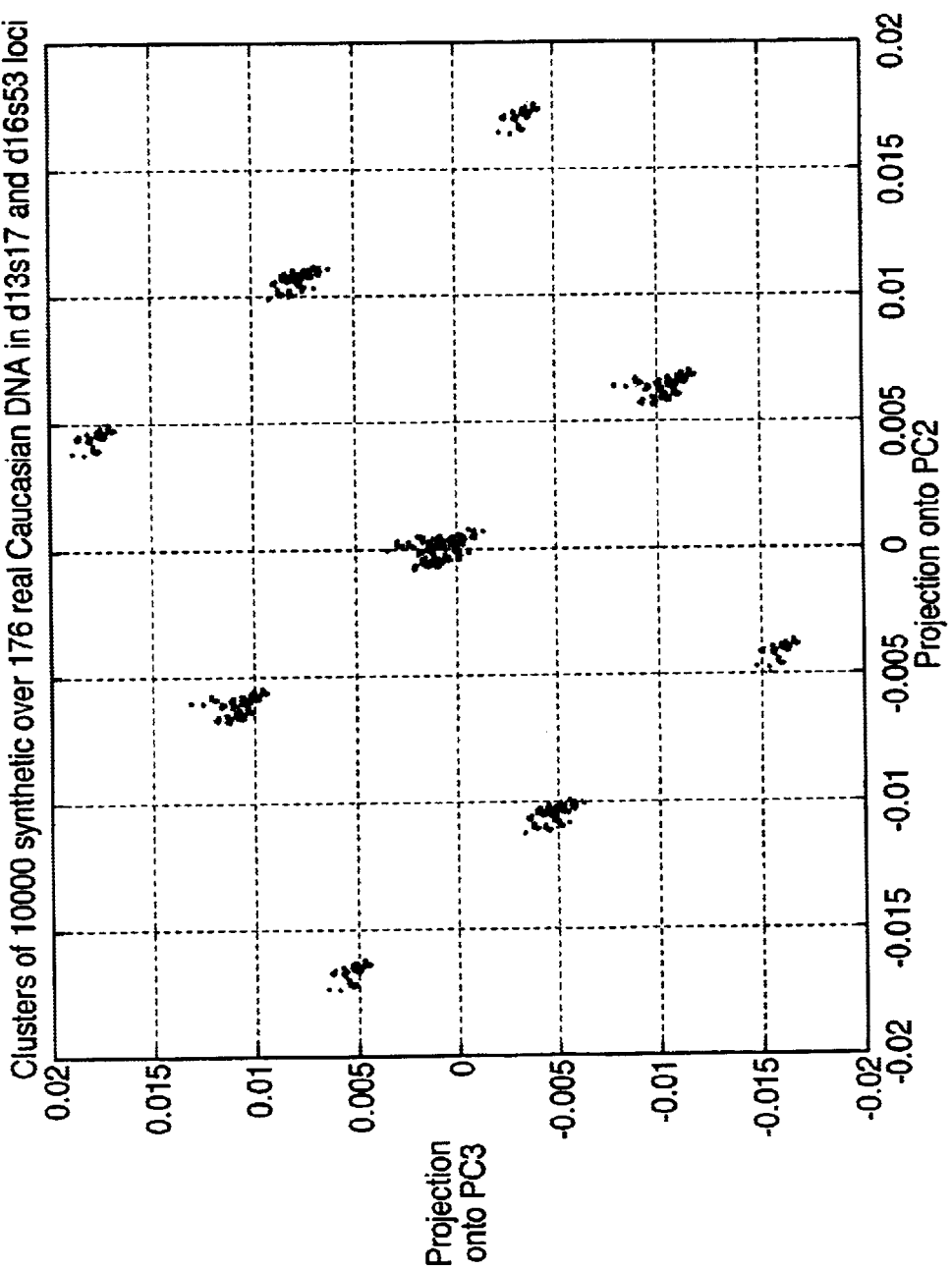

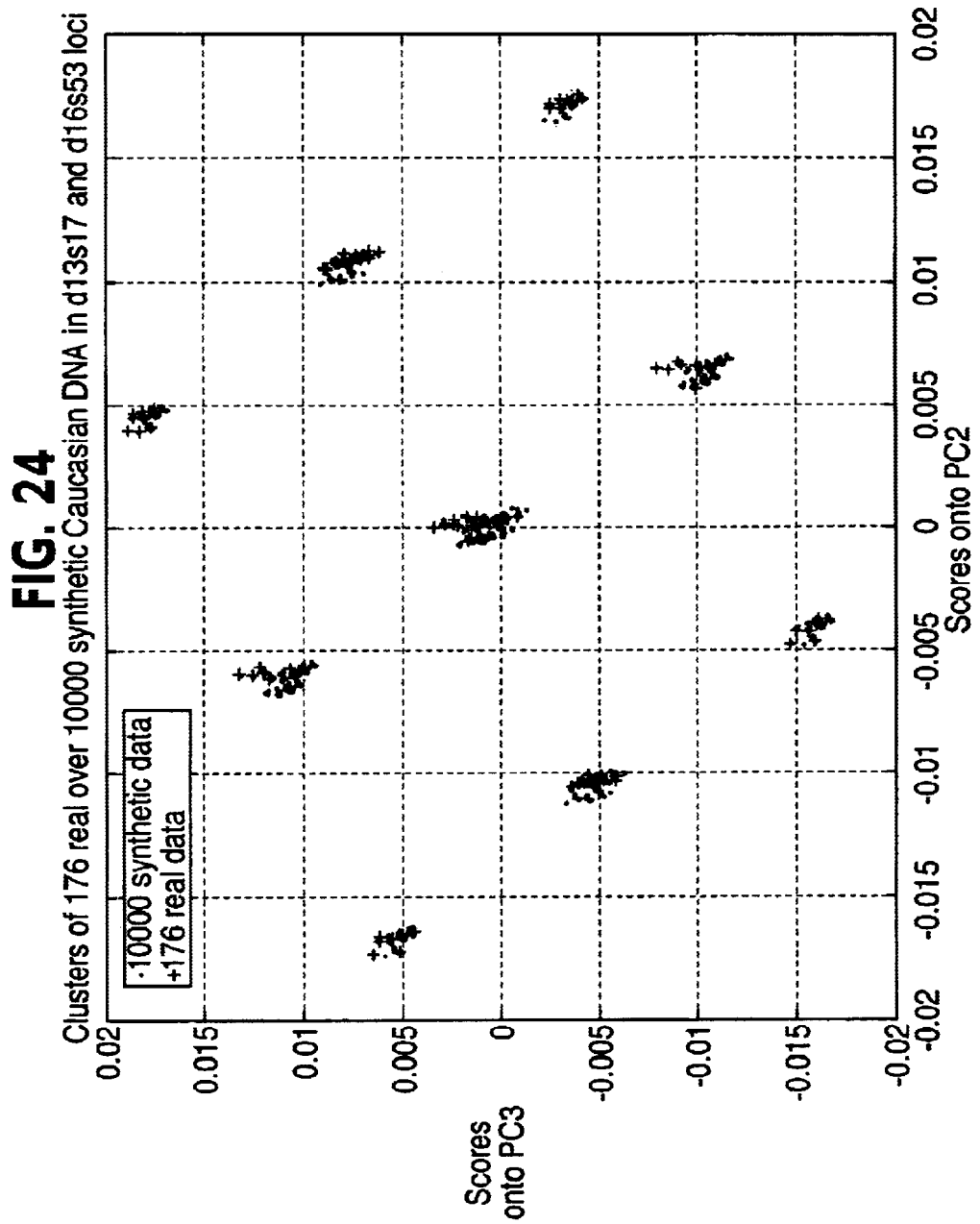

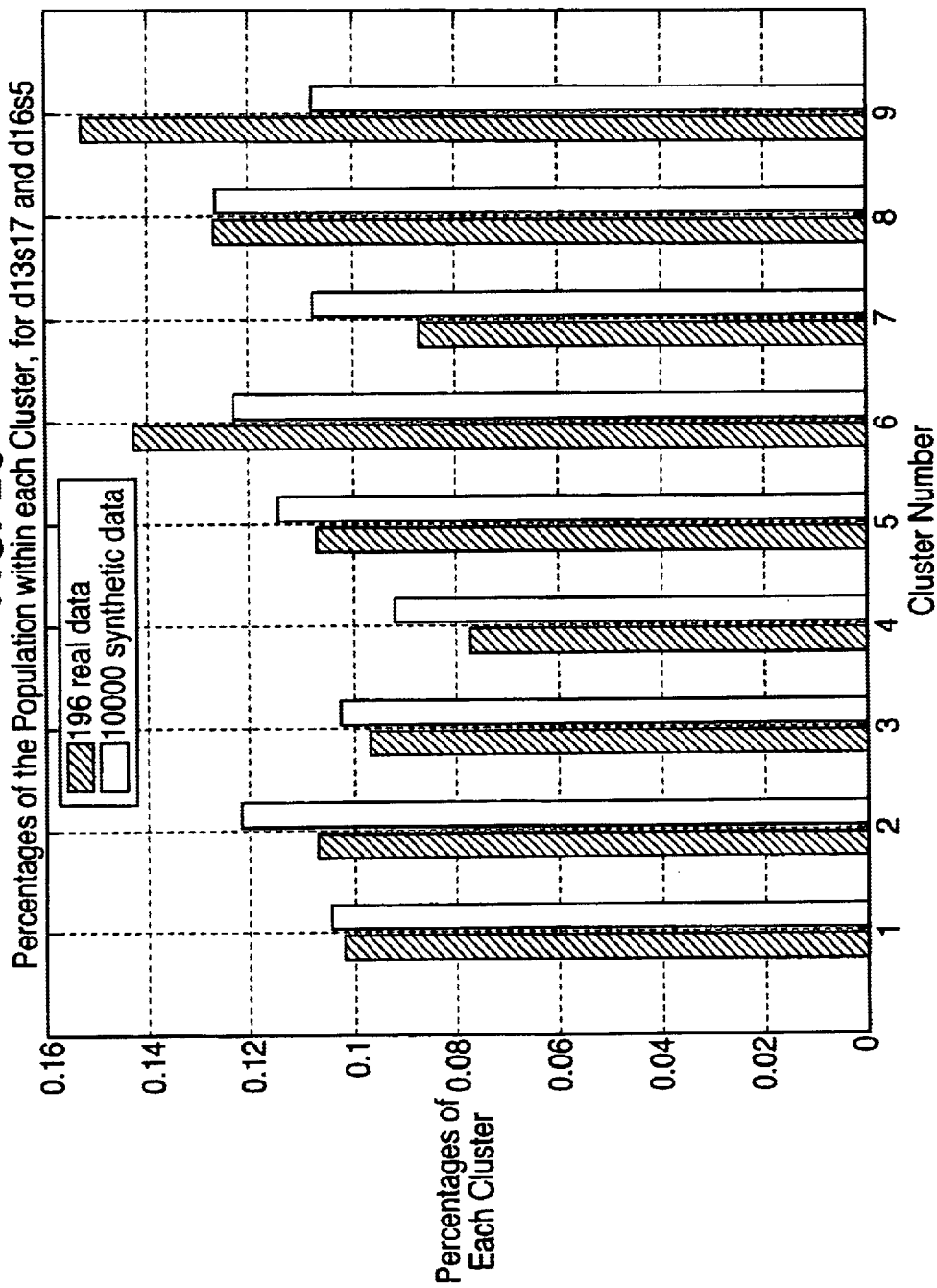

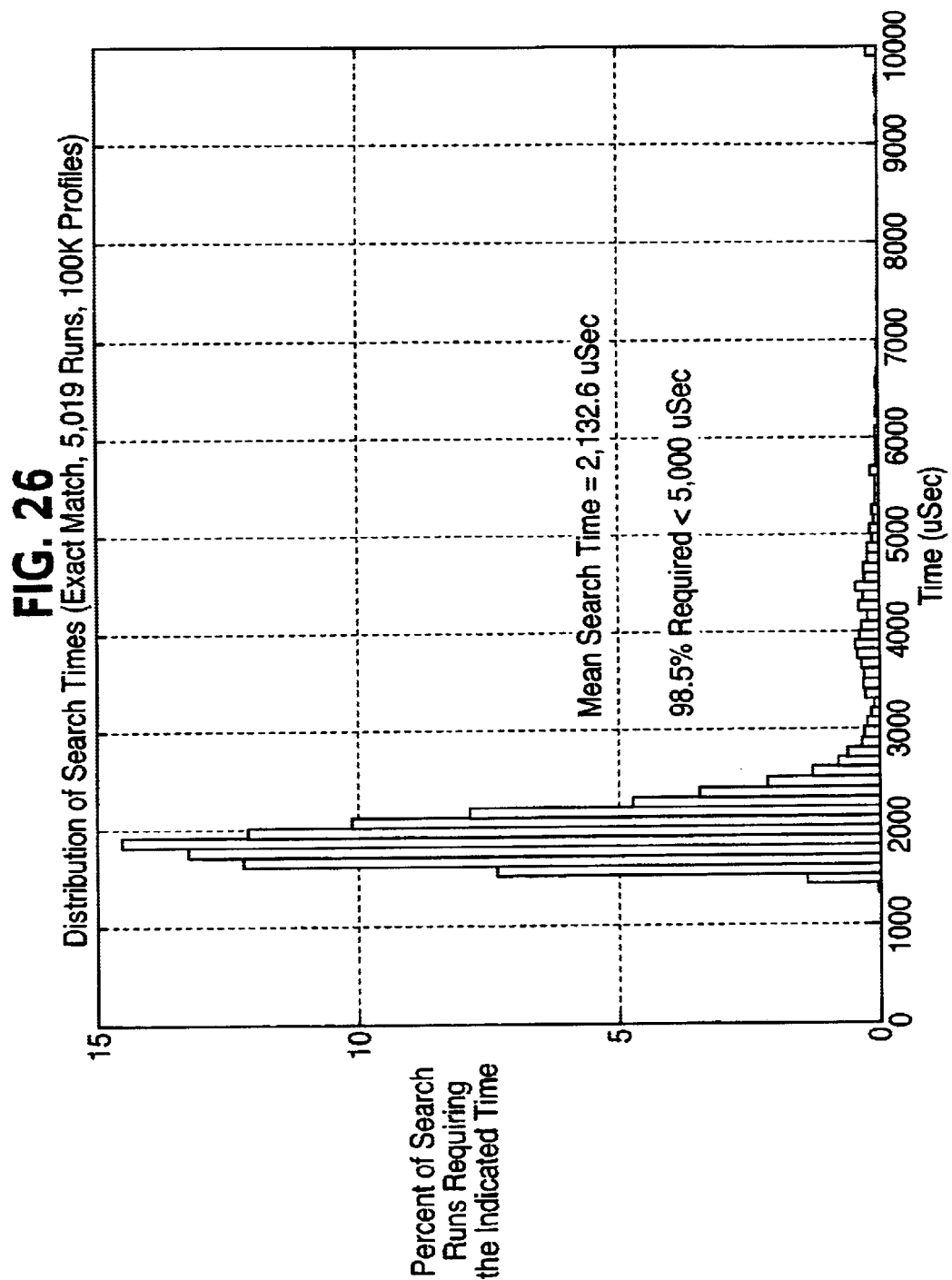

METHOD OF INDEXED STORAGE AND RETRIEVAL OF MULTIDIMENSIONAL INFORMATION

This application claims the benefit of U.S. Provisional Application No. 60/156,452, filed Sep. 28, 1999, which is hereby incorporated by reference in its entirety.

The U.S. Government retains certain rights in this invention due to funding provided by contract J-FBI-98-083 awarded by the Federal Bureau of Investigation.

TECHNICAL FIELD OF THE INVENTION

The invention is related to the area of computer software for the management of databases. In particular it is related to the field of tree-structured indexing methods for the rapid storage and retrieval of DNA profile information from databases containing a large number of records.

BACKGROUND OF THE INVENTION

Existing database indexing methods exploit the structure inherent when more than one database field is used. These methods are commonly based upon space-filling curves to map the multi-dimensional data to a single dimension, which is then indexed in the standard fashion. The B-tree indexing algorithm [1] and similar algorithms attempt to maintain a balanced index tree by adjusting the thresholds used to split the indexed parameter's value set as the tree is descended. Multi-dimensional indexing methods are found under several names, such as R-trees [2] and R*-trees [3], and applications exist in the implementation of image databases and other areas. A parallel database based upon this type of approach has been patented by IBM [4] using MPI, a widely available message-passing interface library for parallel computing [5]. Other implementations exist in some commercial database systems, such as the Informix Dynamic Server's Universal Data Option [6].

DNA profile information consists of allele information at one or more DNA loci or sites. Typically 10 or more loci are used. Typically, individuals can exhibit either one or two alleles at each site; forensic samples containing DNA from two or more individuals can have more alleles. The anticipated size of databases containing DNA profile information necessitates new methods to manage and utilize the stored information. An example of such a database is the national CODIS [11] database, which is expected to eventually store on the order of $10^8$ profiles and uses complex match specifications. Standard database indexing structures such as B-trees, which provide rapid access to records based upon the value of a selected database field, are not able to take advantage of naturally occurring structure in the data. Although more than one field may be indexed, the index structures are computed independently. Retrieval of stored information based upon several indices requires an intersection of the results of retrievals based upon each index, which is a time-consuming operation. Methods using R-trees, R*-trees, and similar approaches rely on space filling curves rather than structural properties of the data. There remains a need in the art for database structures and search engines that can rapidly and efficiently store, manage, and retrieve information from very large datasets based upon the structural properties of the data expressed in multiple fields.

SUMMARY OF THE INVENTION

By way of example and without limiting the application of the present invention, it is an object of the invention to organize the storage of DNA profile information to minimize the time required to locate all DNA profiles within the database that satisfy a set of user-selected criteria when compared against a target DNA profile and therefore match the target.

It is a further object of the invention to provide a method for the parallel implementation of a database of DNA profiles by breaking up the work involved in storage and retrieval of sets of information into many requests for work which may be distributed among a cooperating group of computer hosts to balance the workload across the hosts and thereby minimize the time required to perform the work.

These and other objects of the invention are provided by one or more of the embodiments described below.

One embodiment is a method for performing a retrieval operation in a database comprising a tree of nodes. The tree of nodes comprises a root node which is connected to two or more branches originating at the root node. Each branch terminates at a node. Each node other than the root node may be a non-terminal node or a leaf node. Each non-terminal node is connected to two or more branches originating at the non-terminal node and terminating at a node. Each leaf node comprises one or more data records of the database. A test is associated with each non-terminal node that defines a partition of data records based upon either entropy/adjacency partition assignment or data clustering using multivariate statistical analysis. A current node is initially set to the root node. Input is received of a search request providing a retrieval operation and information necessary to perform the retrieval operation. The test associated with a current node is performed responsive to the search request. The test results in identification of zero or more distal nodes connected to the current node. The identified distal nodes can, according to the test, contain the data record. The test is repeated using an untested distal node which is a non-terminal node as the current node. The retrieval operation is performed on each referenced node that is a leaf node.

Another embodiment is a method of partitioning data records in a computer into groups of roughly equal size. A function is defined of the probability distribution of the values of a designated variable associated with the data records. The function comprises a linear combination of measures of entropy and adjacency. The values of the designated variable are partitioned into two or more groups such that the value of the function is minimized. Each data record is assigned to a group according to the value of the designated variable.

Yet another embodiment is a method of creating a tree-structured index for a database in a computer. The database comprises a tree of nodes. The tree of nodes comprises a root node which is connected to two or more branches originating at the root node. Each branch terminates at a node. Each node other than the root node may be a non-terminal node or a leaf node. Each non-terminal node is connected to two or more branches originating at the non-terminal node and terminating at a node. Each leaf node comprises one or more data records of the database. The tree-structured index comprises one or more tests associated with each non-terminal node. Naturally occurring sets of clusters are identified in the data records of the database. For each identified set of clusters, a test is defined that assigns each data record to a cluster within the set of clusters. Each such test is associated with a non-terminal node, together with an associated set of clusters. One branch is associated with each cluster within the set of clusters. The branch originates at the non-terminal node and forms part of one or more paths leading to leaf nodes comprising the data records assigned to the cluster by the test.

Still another embodiment is a method of organizing the data records of a database into clusters. One or more variables in each data record are represented in a binary form, wherein the value of each bit is assigned based on the value of a variable. A set of variables is chosen from those represented in all of the data records such that principal component analysis of the set of variables yields distinct clusters of the data records. Principal component analysis is applied to a sample of the data records, and two or more principal component vectors are identified, whereby the scores of the sample data records along these vectors form distinct clusters. A test is formulated based on the identified principal component vectors which assigns each data record to a cluster. The test is then performed on each data record, and the data records are organized into clusters.

Another embodiment is a parallel data processing architecture for search, storage, and retrieval of data responsive to queries. The architecture includes a root host processor that is responsive to client queries; the root host processor creates a search client object and establishes an initial search queue for a query. The architecture also includes a plurality of host processors accessible by the root host processor. The root and host processors each maintain a list of available host processors, query queue length, and processing capacity for each processor. The architecture includes a bus system that couples the host processors and one or more memories for storing a database tree comprising nodes and data of a database accessible via the nodes. The processors are capable of executing a set of tests and associate one test with each non-terminal node of a database tree.

Yet another embodiment is another method for search, storage and retrieval of data from a database. A set of tests is defined, and one test is associated with each non-terminal node of a database tree. Each test defines a partition of data of the database according to either entropy/adjacency partition assignment or data clustering using multivariable statistical analysis. A test result is output in response to a query by evaluation of either a Boolean expression or a decision tree.

These and other embodiments provide the art with novel, efficient, and rapid methods for the storage, retrieval, and management of large numbers of data records using indexed databases.

BRIEF DESCRIPTION OF THE DRAWINGS

FIG. 19 shows the makeup of the second principal component for the d13s-d16s data set. Note that the allele index numbers do not correspond to the actual allele number. The tall bars correspond to alleles 11 and 12 of d13s17 and alleles 11 and 12 of d16s539 respectively.

FIG. 20 shows the makeup of the third principal component for the d13s-d16s data set. Note that the allele index number do not correspond to the actual allele number. The tall bars correspond to alleles 11 (−) and 12 (+) of d13s 17 and alleles 11 (−) and 12 (+) of d16s539 respectively.

FIG. 21 shows the fraction of profiles within each PCA scores cluster that has each of the alleles in the d13s17 and d16s539 loci pair.

FIG. 22 displays a comparison of the locations of true cluster centers (*) and the approximate ones (o), which are predicted from the allele distribution patterns at the four dominant allele positions.

FIG. 23 shows the scores plot for both the large synthetic data set and the small real sample set. The scores from the large data set (the dark gray points) completely cover those of the small real sample set.

FIG. 24 shows the scores plot for both the large synthetic data set (medium gray points) and the small real sample set (the black dark points).

FIG. 25 shows a comparison of the fraction of the sample population that is in each of the nine PCA clusters. The first of each pair of bars at each cluster number position denotes that of the large data set (10,000 synthetic Caucasian data records); the second of each pair of bars represents that of the small real data set (176 Caucasian data records).

FIG. 26 presents a histogram of times required to search a database of 100,000 DNA profiles for an exact match to a specified profile (5,019 runs).

DETAILED DESCRIPTION OF THE INVENTION

Figure 1:
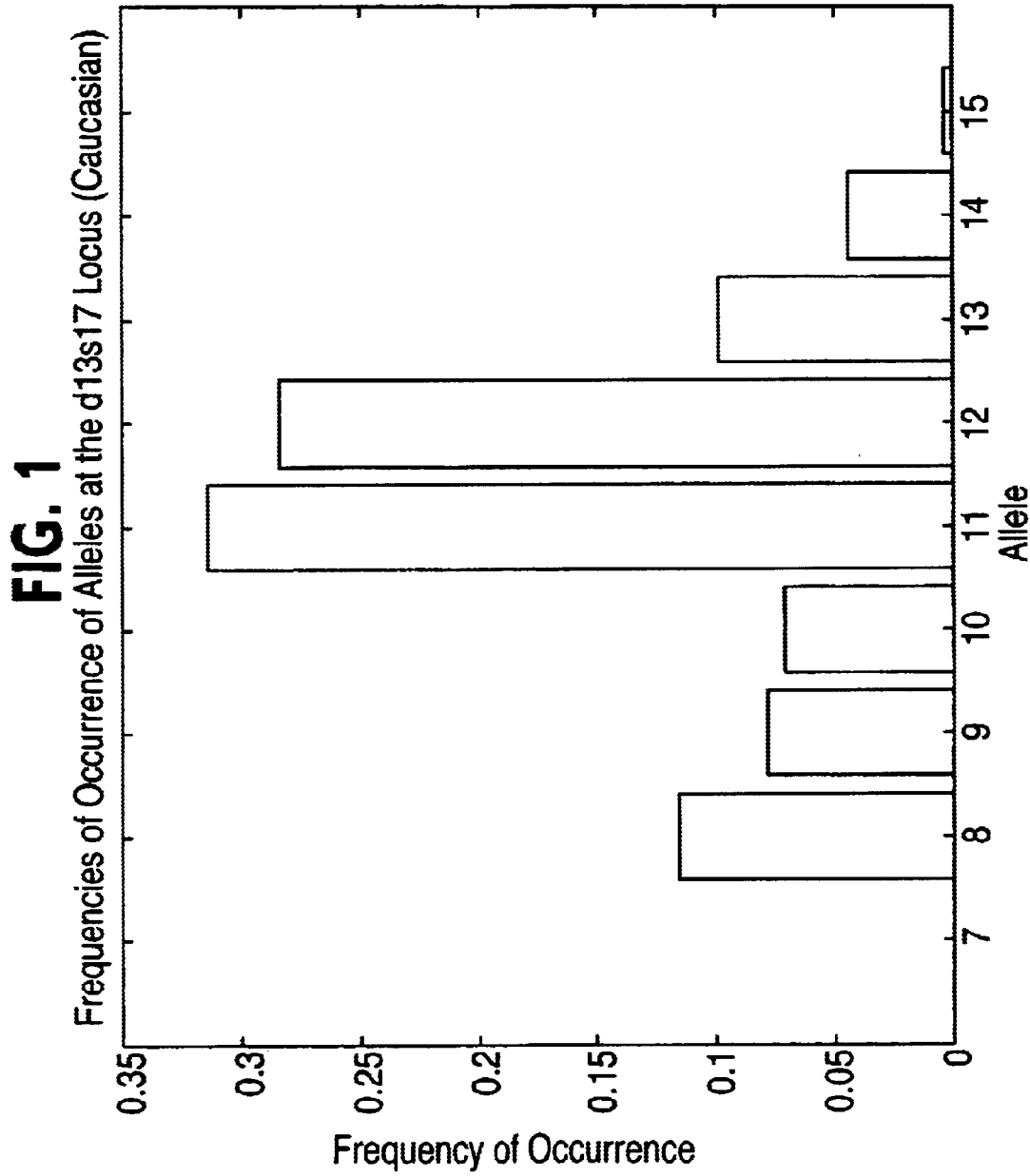
FIG. 1 displays the relative frequency of occurrence of alleles at the d13s17 locus.

The inventors have developed a method of organizing the storage of DNA profile information which minimizes the time required to locate all DNA profiles within the database that satisfy a set of user-selected criteria when compared against a target DNA profile and therefore match the target. The match criteria allow for the possibility of missing allele or locus data, the inexact match of allele information at a specified locus, an error tolerance in the number of base pairs in matching alleles from RFLP DNA locus data, and the specification of equivalent alleles. The match criteria can also define groups of loci that must be present in matching DNA profiles and a maximum number of matching profiles to be returned to the requesting user.

Definitions

A "directed graph" is a pair (N,B), where N is a finite set and B is a binary relation on N. Elements of the set N are called the nodes of the directed graph. A "node" is an element of a set N in a directed graph or tree, such element having connections with branches that either originate from or terminate to the element. The binary relation B is a set of elements of the form $(n_1,n_2)$, where $n_1$ and $n_2$ are elements of N. Elements $(n_1,n_2)$ of the binary relation B are called branches or edges of the directed graph and specify a path from node $n_1$ to node $n_2$. For a directed graph, a "path" is a set of branches $\{(n_1,n_2), (n_2,n_3), \ldots (n_{i-1},n_i)\}$, containing at least one branch that connects node $n_1$ to node $n_2$ defines a path from the originating node $n_1$ to the terminal node $n_2$. The path is said to go from node $n_1$ to node $n_2$. For a directed graph a node $n_2$ is "reachable" from node $n_1$ if a path exists that originates at node $n_1$ and terminates at node $n_2$.

A "tree" is a directed graph that satisfies two properties: (1) for any two nodes $n_1$ and $n_2$ a path exists from node $n_1$ to node $n_2$, or a path exists from node $n_2$ to node $n_1$, (the graph is connected); and (2) no two nodes $n_1$ and $n_2$ exist for which paths exist from node $n_1$ to node $n_2$ and from node $n_2$ to node $n_1$ (the graph is acyclic). For purposes of the invention, a tree can be either a directed graph or an undirected graph. The "root" or "root node" is the unique node of a tree that is not a terminal node for any path in the tree. A "non-terminal" or "non-terminal node" is a node of a tree that is an originating node for at least one path in the tree. A "leaf" or "leaf node" is a node of a tree that is not a non-terminal node. A "subtree" of a tree (N,B) is defined uniquely by any node $n_r$ of the tree, and is the tree $(N_s,B_s)$ formed of the set $N_s$ containing the node $n_r$ and all nodes $n \in N$ that are reachable from node $n_r$, and the set $B_s$ containing all branches that are in paths in the tree that originate at node $n_r$. Node $n_r$ is the root node of the subtree $(N_s,B_s)$. As referred to herein, a "node" can be a carrier of information or data.

For purposes of the invention, any information or data may be optionally contained in, referenced by, attached to, or associated with any node or branch of a tree or directed graph. When a node has a specific structure which determines how information may be contained in, referenced by, attached to, or associated with the node, the node is referred to as a Node object or Node (capitalized).

Additional background information about directed graphs and trees can be found in reference 1 at pp. 86–97.

Search and Retrieval Operations in DNA Profile Databases

It is intended that the claimed invention can be used with any appropriate database. The application of the invention to databases containing DNA profile information is preferred. In the description that follows, the CODIS system is used by example only and is not intended to limit the scope of the invention.

Estimates of the relative frequency of occurrence of each possible allele at each locus are known for various population subgroups. The relative frequency distribution is typically not uniform. The current invention exploits this non-uniformity to improve the efficiency of DNA profile databases. A table can be created of the known alleles that may be present at a specific locus and their relative frequency. One such table for the d13s17 locus, based upon FBI CODIS data, is shown in Table 1. For this locus, there are two alleles (11 and 12) that have significantly larger fractions (frequencies of occurrence) than the others. This is easily seen in FIG. 1. Non-uniform allele frequency structure is apparent at several loci. The database search engine described here exploits such non-uniformity using a "divide-and-conquer" strategy.

TABLE 1

Relative frequency of occurrence of alleles at the d13s17 locus.

| Bin | Allele | Fraction |
| --- | --- | --- |
| 1 | 7 | 0.000 |
| 2 | 8 | 0.115 |
| 3 | 9 | 0.078 |
| 4 | 10 | 0.070 |
| 5 | 11 | 0.313 |
| 6 | 12 | 0.283 |
| 7 | 13 | 0.098 |
| 8 | 14 | 0.043 |
| 9 | 15 | 0.003 |
| Total | | 1.000 |

Figure 2:
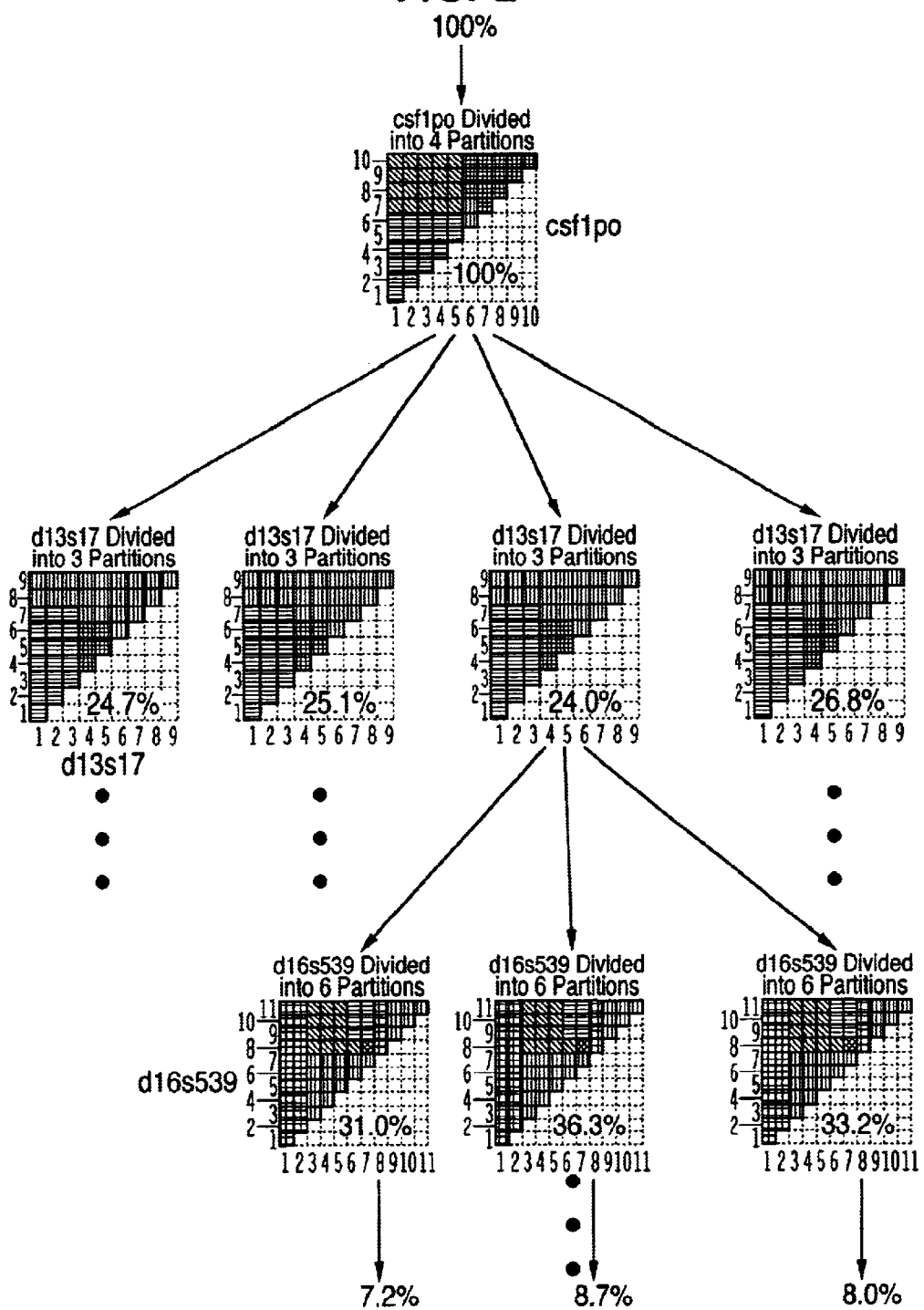
FIG. 2 presents a schematic representation of a tree-structured database.

A tree-structured information storage scheme is shown in FIG. 2. At each node of the tree, beginning at the top (root) node, a test is made upon DNA profile information (either used as a target for a search request or to be stored in the database). Based upon the test results, one or more branches are selected that originate from the node and terminate at child nodes where a new test is conducted. In this manner, portions of the database are ruled out of consideration at each level, narrowing the scope of the search. The complexity of the search method that results is on the order of log(N), where N is the number of DNA profiles stored in the database.

For this to be effective, test results associated with the database tree's nodes need to depend upon information at more than one locus of the DNA profile. In addition, the tests need to be chosen in a manner that causes the resulting tree to be balanced. This means that all paths from the root to leaf nodes where DNA profiles are stored are roughly the same length. This causes the portions of the database contained in the subtrees rooted at nodes at each level of the tree to be roughly the same size, as is shown in FIG. 2 where the percentage of DNA profiles in the database referenced by each node of the tree is shown at that node.

The tree structure of the database has the additional benefit of being parallelizable. Each branch leading from a node that is chosen as a result of a test can be assigned to an independent computer host or processor, allowing exploration of the tree during a search to proceed on multiple computer hosts in parallel. In the illustrated database in FIG. 2, each of the three bottommost nodes can be assigned to a different computer, resulting in three roughly equal search problem sizes.

A unique feature of the method described here is its use of a priori information about the statistical distribution of DNA profile information to ensure that the database tree is balanced.

Search and Retrieval Operations in Other Database Types

The multivariate statistical clustering method and information storage and retrieval methods that utilize this can be applied to other forensic science applications. These applications include the categorization and classification of any forensic evidence sharing one or more attributes. For example, these methods can be used to compare the events and construction technologies describing improvised explosive and incendiary devices (bombs). The multivariate statistical clustering method will reveal similar cases presented to an existing bomb incident database. In this embodiment, clusterable variables include the presence or absence of various types of explosives, methods of construction, and ancillary devices such as timing devices and other triggers. This type of database is beneficial for determining patterns in similar bombs constructed by the same individual(s) as well as circumstances surrounding their placement, the target, and the motive of the bomber. Other forensic applications include psychological and personality profiles of criminals, descriptions of stolen artwork, indexing, storage, and comparison of forged documents, linguistic content of threatening communications, image comparisons of spent bullet and cartridge cases, photographic images of crime scenes, determination of authorship of copyrighted works, and the content of computer hard drives.

Beyond forensic applications, these methods are applicable in any domain of knowledge where information to be stored, indexed, retrieved, and compared can be characterized by the presence or absence of common features. Suitable application domains include maintenance of image databases, such as arrest photos and catalogs of identifying marks (scars, marks, blemishes, and tattoos). In agriculture, image databases are maintained of crop pests, and an important application is the rapid identification of pests on samples of infested plants. In planetary science, image databases are maintained of landforms and features taken from both space and air platforms, and the rapid identification of an image of a location on the earth's surface is important. In these application domains it is possible to extract image features that can be coded by their presence or absence, allowing the utilization of the multivariate statistical clustering method and related database methods. Within each category of feature, the features may be typed by degree, such as physical size, color attributes, and texture. This typing admits the application of entropy/adjacency partition assignment methods as a mechanism for partitioning a collection of information in order to facilitate rapid comparison, access, and retrieval.

Another application domain is the storage of references to textual information. Representation of text documents by vectors indicating the presence or absence of words and phrases, which may then provide indexing structure through the use of multivariate statistical clustering and data access methods. Locations of words and phrases within a document, as well as the relative positions and frequencies of these words and phrases, enable the utilization of the entropy/adjacency partitioning method and related database indexing structures. These types of representation have been utilized with singular value decomposition and QR factorization for text storage and retrieval [14]; however, the methods described herein use clusters derived from multivariate statistical analysis to partition the database and form a database tree. Wherever the application provides a natural association of the representations of quantities such as measurements of word positions and frequencies with a distance or similarity measure of association between data records, database trees utilizing entropy/adjacency partitions can provide highly efficient methods for identification of records most similar to a target record referenced by a search request. In these and other applications where a binary encoding of information relating to the presence or absence of data features is appropriate, database trees utilizing clustering based upon multivariate statistical analysis can provide highly efficient methods to implement database indexing, search, and retrieval strategies. In most applications, a combination of these methods can be utilized.

The above disclosure generally describes the present invention. A more complete understanding can be obtained by reference to the following specific examples, which are provided herein for purposes of illustration only and are not intended to limit the scope of the invention.

EXAMPLE 1

Database Implementation

A key to implementation of the search specification on a tree-structured database is what occurs at the nodes of the database tree. These nodes can be C++ objects and can contain partition objects used to describe how the database is segmented at each node. Two types of partitioning at the nodes are illustrated: entropy-adjacency partition assignment and data clustering using multivariate statistical analysis. The database is implemented using a Search Queue and one or more Search Engines in each computer host in a single or parallel computer environment. The Search Queue holds Search Requests and additional information such as requests to store or delete DNA profile information in the database. The Search Engines take elements from the Search Queues and perform the requested activities. During this process, additional Search Requests may be generated, which each Search Engine places in the Search Queue. The CODIS search engine communicates with clients that request service across a network interface, and returns the requested information to these clients. This process is shown schematically in FIG. 3 for the single host case. Multiple hosts in a parallel computing environment are accommodated using multiple communicating copies of this process. The hosts can either all operate on the same database, or each can contain a portion of the database; a mixture of the two methods can also be used. As an example, communicating groups of processors may operate where all members of each group are assigned the same portion of the database.

Figure 3:
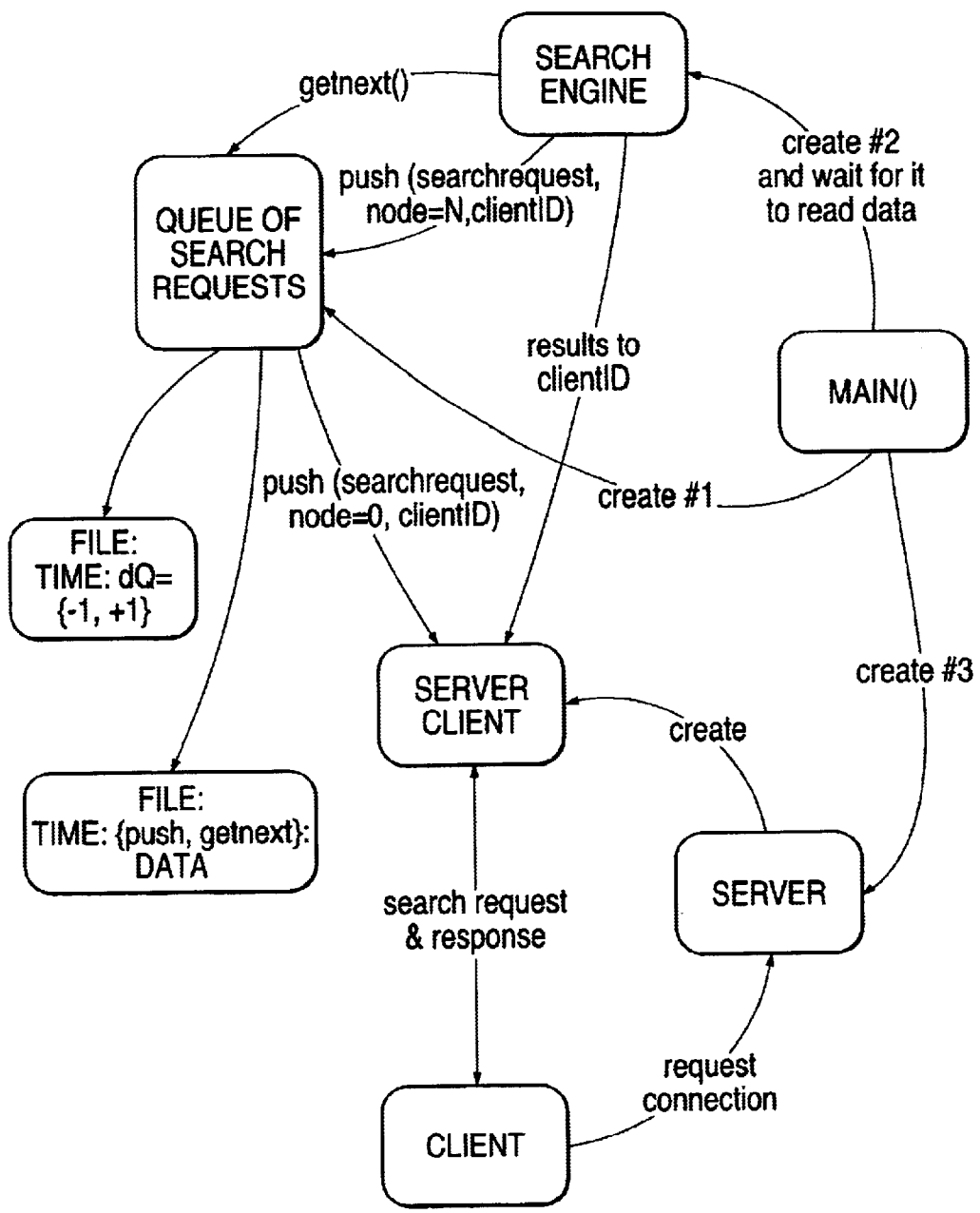
FIG. 3 shows a schematic representation of a search server residing on a single host computer.

In FIG. 3, the client initiates a request for service with the Server, which is a computer process whose sole function is to broker exchanges between clients and the CODIS search server. Upon receipt of a connection request, the Server instantiates a Server Client, which is a computer process or thread dedicated to servicing the client. If the client is initiating a request to search the database, information necessary to define the Search Request is transmitted from the Client to the Server Client, and the Server Client assembles a Search Request and inserts it in the Search Queue (labeled "Queue of Search Requests" in FIG. 3).

A Search Engine removes the topmost (oldest) Search Request from the Search Queue when it becomes available. The Search Request specifies an identifier for the requesting Client, an associated node of the database tree at which the search is to begin, and a set of target DNA profiles and related information specifying the context of the search. If the database tree node is not a leaf node (has descendents), the Search Engine can use one of the available partitioning methods to determine which nodes at the next lower level of its database tree must be searched. If the node is a leaf node, the Search Engine searches the set of DNA profiles stored at the node for matches. This process may either generate additional Search Requests or matching DNA profiles. Search Requests are placed on the Search Queue, and matching DNA profiles are returned to the Client. The Search Engine can follow one branch to a next lower node and repeat the process in order to achieve higher performance rather than insert the corresponding Search Request onto the Search Queue. The Search Engine block in FIG. 3 is schematically shown as a single process or thread, but it should be understood to represent one or more Search Engines on a single computer host.

Various methods can be utilized to balance the loads of the computer hosts so that the average waiting times for service and computation in Search Queues and Search Engines across all hosts are equalized. For example, blocks of Search Requests can be exchanged among hosts from hosts with relatively long average waiting times to hosts with shorter waiting times. A stochastic scheduling method can be utilized, causing hosts with relatively short waiting times to, on average, receive more exchanges than hosts with longer average waiting times. The sizes of the blocks exchanged can be adjusted to accommodate the relative speeds of the processors and the inter-processor communications protocols and hardware. Either of two software packages used for parallel computing, MPI [5] and PVM [7], or other similar packages, can be used to implement the balancing method.

The Main block shown in FIG. 3 starts the execution of the Server, Search Queue, and Search Engines on a computer host and initialized the environment to allow these processes to communicate with other hosts participating in the parallel computer environment. In addition, various log files can be generated to aid in debugging problems and tracing utilization of the CODIS search server; two of these are shown in the figure.

EXAMPLE 2

Entropy-Adjacency Partition Assignment

To minimize worst-case search time, division of the database into N roughly equal portions at each level of the database tree is highly desirable. A simple and fast test is needed to accomplish this. One test method that can be used to accomplish this is entropy-adjacency partition assignment. This method assigns members of the set of possible allele pairs at a specified locus to groups. The goal is to choose these groups so that their expected sizes are roughly equal, and so that alleles with indices that differ by a small number (corresponding to the number of repeated sequences for STR DNA profiles and the number of base pairs for RFLP DNA profiles) have a high probability of being assigned to the same group. By preferentially assigning alleles differing by a small number of base pairs to the same group, the growth of the number of generated search requests due to a client's specification of equivalent alleles will be less than would be the case for other assignments.

Figure 4:
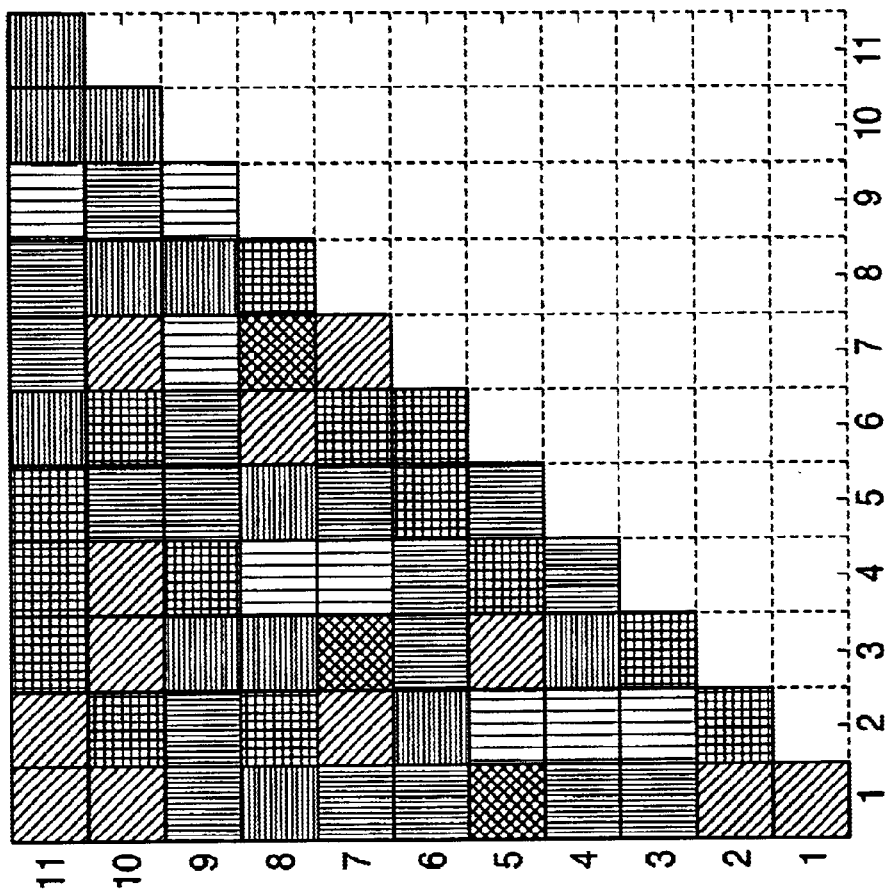
FIG. 4 shows a minimum entropy partition membership assignment for the d16s539 locus.

The set of possible allele pairs at a locus can be viewed as a two-dimensional grid, where each row or column corresponds to an allele. Since the pair (allele1, allele2) is the same as the pair (allele2, allele1), any partition assignment on this grid is symmetric. Thus, only half need be shown. A partition assignment that minimizes the entropy of the resulting partitions is shown in FIG. 4 for the d16s539 locus. In the figure, different shadings of gray (colors can also be used) correspond to different partition membership assignments. The axes are labeled with the sequence numbers of the d16s539 alleles; the alleles range from 5 to 15 inclusive. Entropy is a concept from information theory, and for the partition assignment problem minimum entropy is equivalent to creating a partition whose members are as close as possible to the same size (expected number of elements). From the figure, it is apparent that minimum entropy assignment does not tend to assign adjacent allele pairs to the same partition member.

The partition assignment problem can be solved by a global optimization procedure based upon simulated annealing. In this method, an initial random assignment is chosen, and its cost (entropy) is calculated. The assignments are represented by non-negative integers. In the figure, a division of the allele pairs into six partition members is desired, and the members are labeled with the integers 0 through 5, inclusive. The optimization procedure randomly chooses an allele pair to modify and randomly chooses a proposed new assignment for that pair. The change in cost that would result if the new assignment were used is calculated, and if the cost decreases the proposed change is accepted. If the cost increases the proposed change is accepted with a probability p that begins with unity and declines monotonically with iteration number as the optimization process proceeds. An exponentially decreasing probability of acceptance (a geometric sequence) has been found to work well in practice. The optimization procedure terminates when either the cost has not been further decreased over a specified number of iterations or a maximum number of iterations has been achieved. The last computed assignment is used as the solution to the problem. A variation of this procedure, which is used in the Examples, is to maintain a copy of the best (lowest cost) assignment achieved through the current iteration, updating this as better assignments are found, and to use the last best assignment as the optimal assignment.

Preferential assignment of adjoining allele pairs can be achieved by introducing a cost associated with the absence of adjacency. For every allele pair (A), the four (less on the boundaries) assignments for allele pairs that differ by one index in one allele are examined, and a count variable is initialized to zero. For every assignment that differs from the assignment of allele pair (A), a one is added to the count variable. The count variable is then scaled by the probability of the allele pair's occurrence, and these scaled values are summed over all possible allele pairs to form the adjacency cost. An allele pair with zero probability of occurrence can allow the assignment of that pair to be arbitrarily made without regard to adjacency. To avoid this problem, a small number can be added to the probabilities of occurrence, or to those that are zero, causing the assignment to affect the cost. The results reported herein utilized a value of 0.005 added to all allele pair probabilities of occurrence. The resulting adjacency cost is linearly combined with the entropy cost, and the combined cost is minimized using the global optimization procedure. This can be expressed by the equation $$Cost = Entropy + Weight * Adjacency$$

where Entropy is the cost due to the non-uniform size of the partition members, Adjacency is the cost due to the existence of adjacent allele pairs having different assignments, and Weight is a non-negative number defining the relative importance assigned to the adjacency cost.

Figure 5:
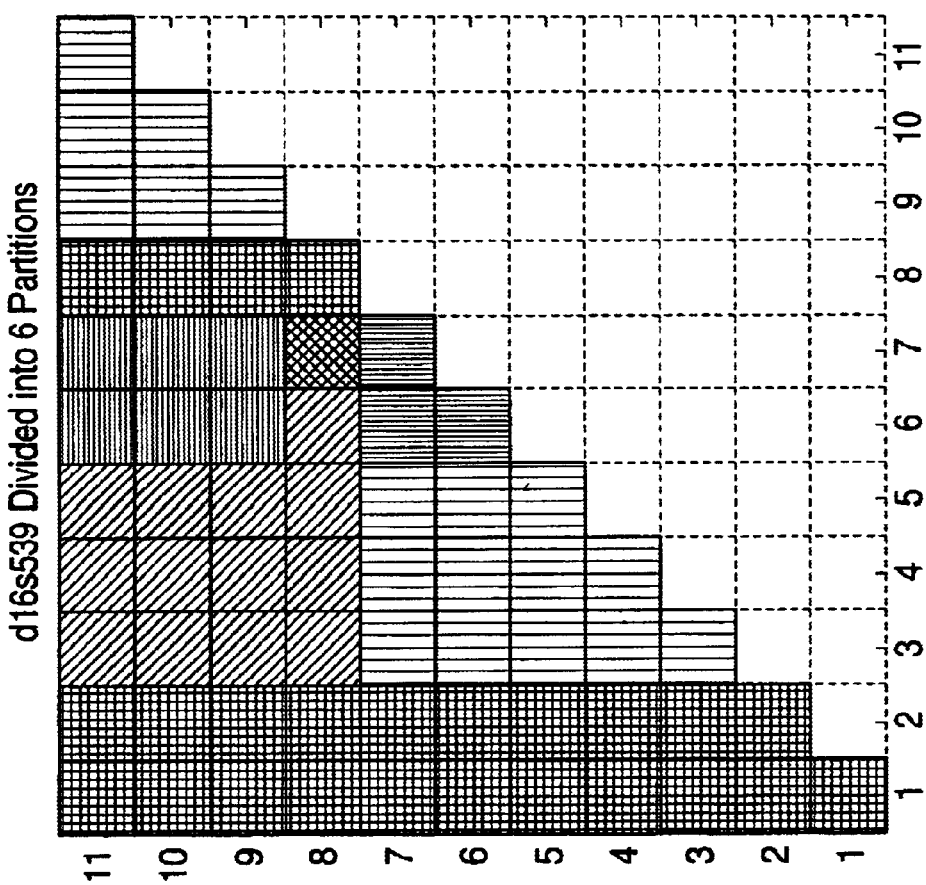
FIG. 5 shows a minimum entropy/adjacency partition membership assignment for the d16s539 locus.

For certain linear combinations, this cost function results in adjacent groups of allele pairs being assigned to the same partition member without drastically impacting the entropy (measure of non-uniform partitioning) of the result. This effect can be seen visually in FIG. 5, where the allele pairs of locus d15s539 are partitioned into six groups. For this partition assignment the entropy is 1.01201, whereas for the assignment shown in FIG. 4 the entropy is 1.0111.

Figure 6:
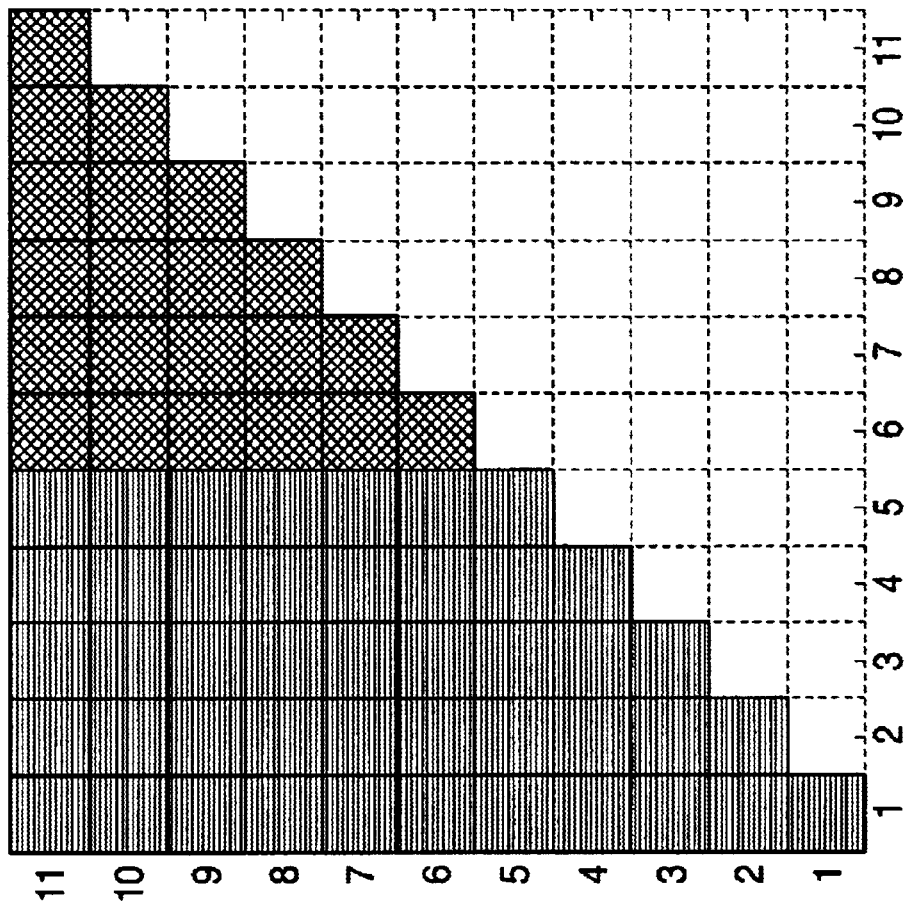
FIG. 6 shows a minimum entropy/adjacency partition membership assignment for the d16s539 locus where too great a weight is afforded the adjacency cost.

This process can be carried to an extreme by weighting the adjacency cost too heavily. In this case, the number of partition members decreases with some members containing zero elements. This effect is visible in FIG. 6. At the present time a precise way to select the "best" trade-off between entropy and adjacency is not known. If minimization of entropy cost is too heavily favored, search performance using equivalence and RFLP error tolerances will be adversely affected. If adjacency is too heavily favored, the database tree will be become unbalanced, resulting in "long legs" and poor worst-case performance. "Engineering judgment" can be used to select a partition map (via the weight) from many computed solutions that will yield acceptable performance. This can be done by computing optimal solutions to the assignment problem for a variety of non-negative weights. If the weight is too large not all partitions will contain assigned allele pairs. If the weight is too small assignments similar to those shown in FIG. 4 will be observed. Iteration may be required to determine suitable values.

EXAMPLE 3

Database Design Using Entropy-Adjacency Partitions

A schematic representation of the database tree was presented in FIG. 2. In that figure, each node of the tree is represented as being implemented using an entropy-adjacency partition. In practice, this is only one of two methods that may be used at a node, and the tree may contain a mixture of the two cases. The implementation of the tree nodes using entropy-adjacency partitions will be discussed in detail in this section; however, the implementation of the tree nodes can also be accomplished using data clustering.

Figure 7:
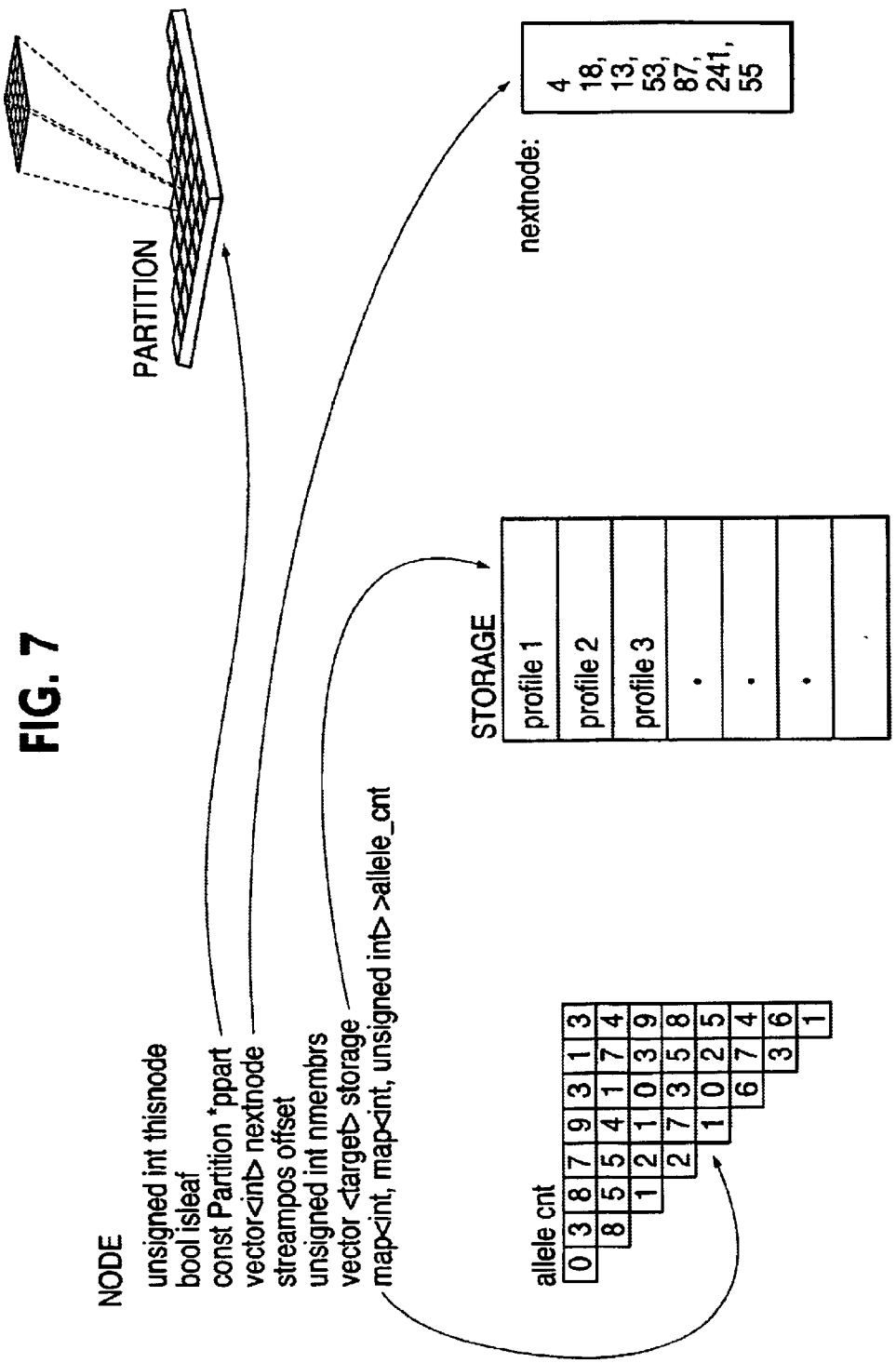
FIG. 7 presents a schematic representation of the C++ Node object.

A decision tree node can be implemented by a C++ Node object, as shown schematically in FIG. 7. The object can contain a unique identifying integer stored in the thisnode parameter. A Node object may be either a leaf or non-leaf (non-terminal) tree node, as specified by the Node data element isleaf. If it is a leaf, the node can store DNA profile information located at that portion of the tree in a storage data structure. As DNA profiles are being stored into the database, a threshold is utilized to determine at what point a leaf node should be converted to a non-terminal node, resulting in two or more nodes one level below the node. Nodes can track the total number of DNA profiles they reference in the nmembers parameter. The offset parameter can be used when stored DNA profiles are located out of processor memory, for example on a disk drive to locate the information relative to the start of the storage media.

Non-terminal Node objects can maintain a list of nodes (nextnode), referenced by the locations of the corresponding Node objects in an array, that can be reached by branches from the nodes and are one level below the nodes in the database tree. Nodes based upon entropy-adjacency partitions can contain a pointer to a C++ Partition object (ppart), which can implement the data structures and methods necessary to utilize the partition information. For each allele pair associated with a partition, a count of DNA profiles matching that allele pair can be maintained by the Node object in the allele cnt map. This information can be utilized to avoid searches along branches from the node that contain no DNA profiles capable of matching a target DNA profile.

Figure 8:
FIG. 8 provides a schematic representation of the C++ Partition object.

A C++ Partition object can be used to store entropy-adjacency partition assignment information. A Partition object defines which subset of the database associated with the database tree node a profile belongs in. These objects are represented schematically in FIG. 8. A string identifying the locus used for the partition can be stored in a name entry. A nmembers entry can specify the number of groups in the partition. Missing allele pair values can be accommodated; a probability of the occurrence of missing data can be maintained in a pmissing entry. A vector of probabilities of occurrence, one for each possible allele, can be maintained in a popstat structure. The table of partition assignments, along with the probabilities of occurrence of each allele pair, can be maintained in a table map. Each entry of this map is a PartEntry object containing the assignment and probability.

Partitions can be used by many database tree nodes and are therefore not usually included within the Node objects. Rather, a pointer in the Node objects can be maintained to the appropriate Partition object. The Nodes can be stored in an array in a predetermined order which is consistent across all hosts participating in the parallel machine, allowing Search Requests to be exchanged across host boundaries.

EXAMPLE 4

Mapping Match Specifications to Methods

The CODIS system provides detailed specifications [11] governing how two DNA profiles may match. A matching algorithm used with CODIS must correctly account for:

PCR allele equivalence,

RFLP measurement error,

Match stringency on a per-locus and per-profile basis,

Mismatch on a maximum allowed number of loci,

Matches on a minimum number of loci,

Completeness, and

The maximum number of DNA profiles to be returned in response to a search request.

Most of these specifications can be interpreted using locus partition and search state information.

Figure 9:
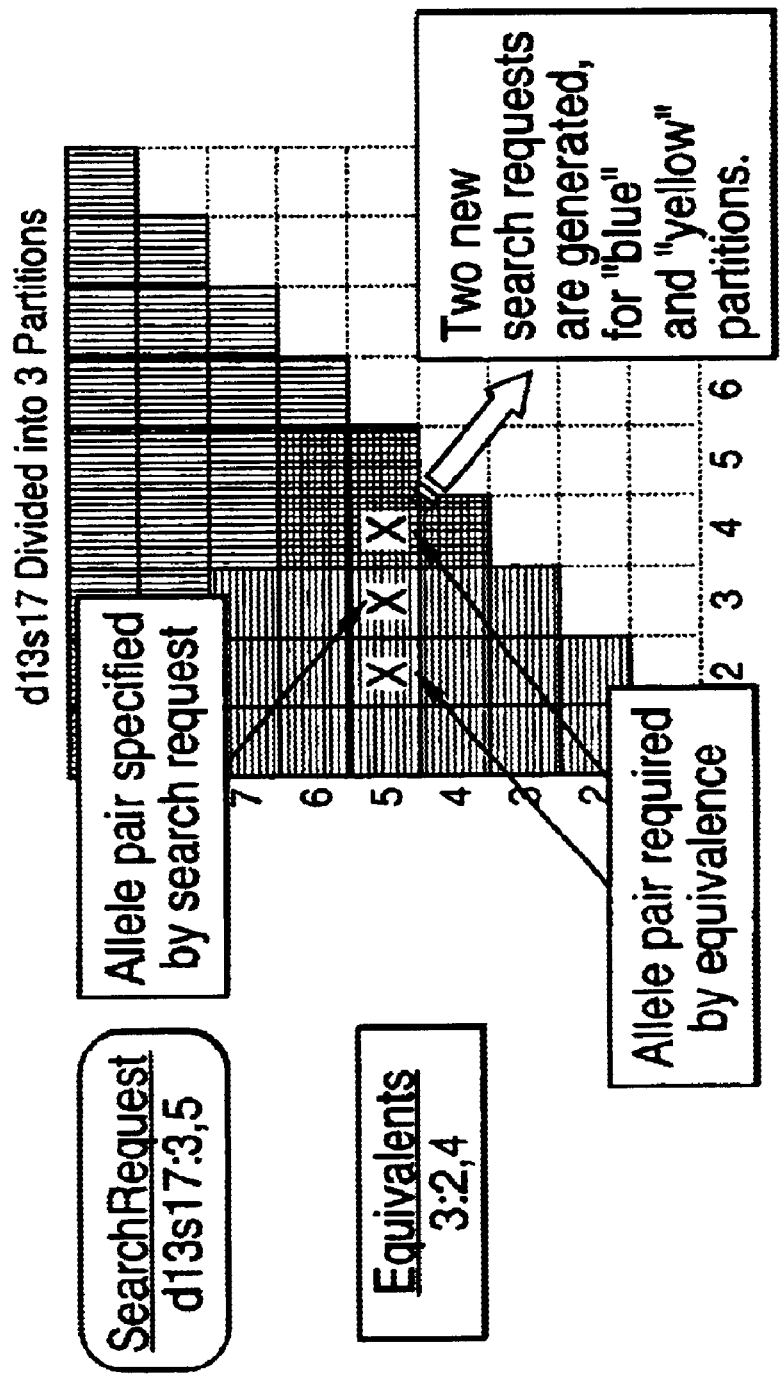
FIG. 9 demonstrates the effect of allele equivalence.

Search Requests can be evaluated by the C++ Node objects. The node can use the Search Request's stored information, along with the partition information referenced by the Node, to generate results, which are returned to the requesting Client, or new Search Requests. Results are only generated when the Node object is a leaf node and contains DNA profiles. If PCR alleles at a locus are declared equivalent, then a DNA profile target provided by a Search Request that contains one of these alleles must match all of the equivalent alleles as well. This is shown in FIG. 9 where the Search Request contains a target profile with allele information for locus d13s17 (alleles 3 and 5), and declares that alleles 2 and 4 are equivalent to allele 3. The yellow (lighter) "X" in the figure corresponds to the allele pair (3,5) and is located in the partition assignment designated by the blue shading. The pink (darker) "X"'s in the figure correspond to the allele pairs (2,5) and (4,5), both of which also match (3,5) because of the declared equivalence. Since the allele pair (4,5) is assigned the partition designated by the yellow (light) shading, two new Search Requests are generated (assuming the allele_cnt table entries are positive) for the "blue" (dark) and "yellow" (light) partitions.

Figure 10:
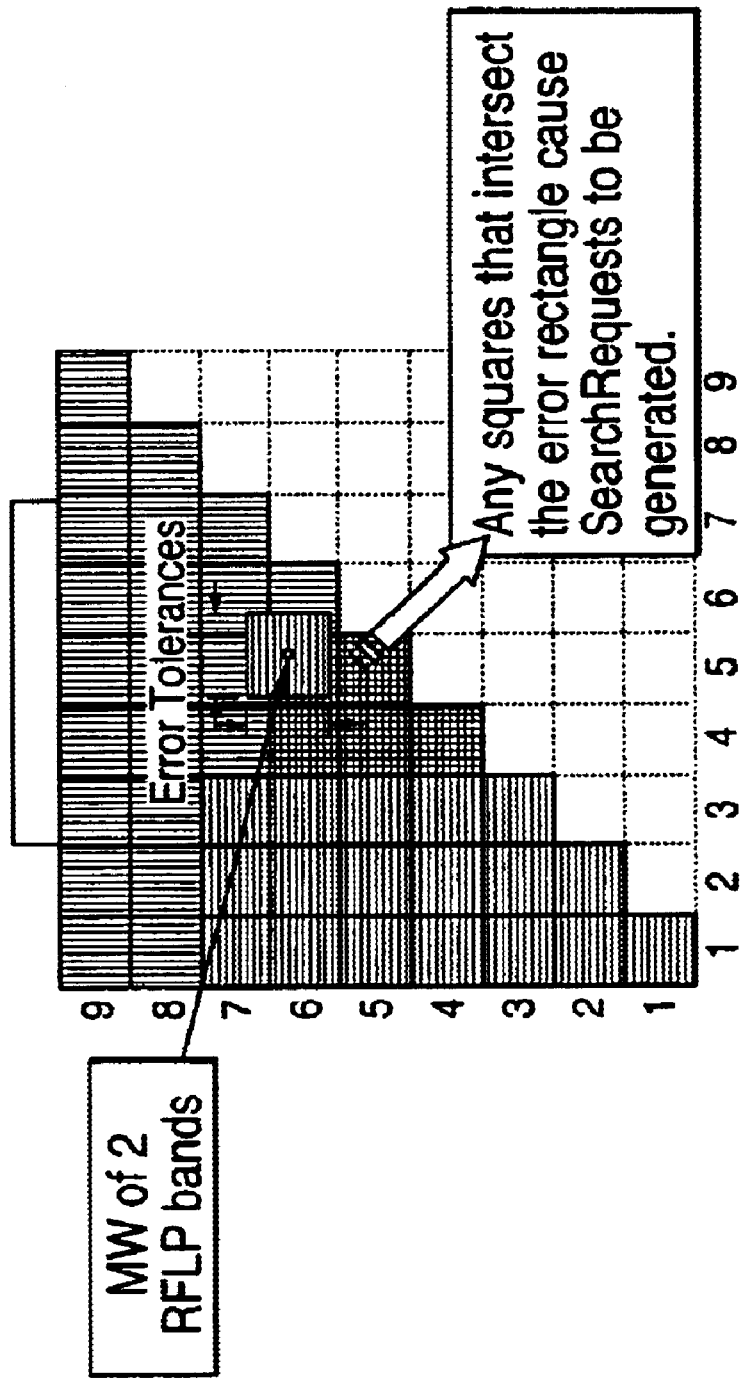
FIG. 10 illustrates the effect of RFLP measurement error.

The search behavior induced by RFLP measurement error is similar to the case of PCR allele equivalence. Measurement error in CODIS is represented by percent relative error bounds on the stored values of RFLP bands. The result is a region (represented by a square in the next figure) within which a band is required to match RFLP DNA target information. Any squares representing ranges of stored RFLP data that intersect this region can cause new Search Requests to be generated, as shown in FIG. 10.

Figure 11:
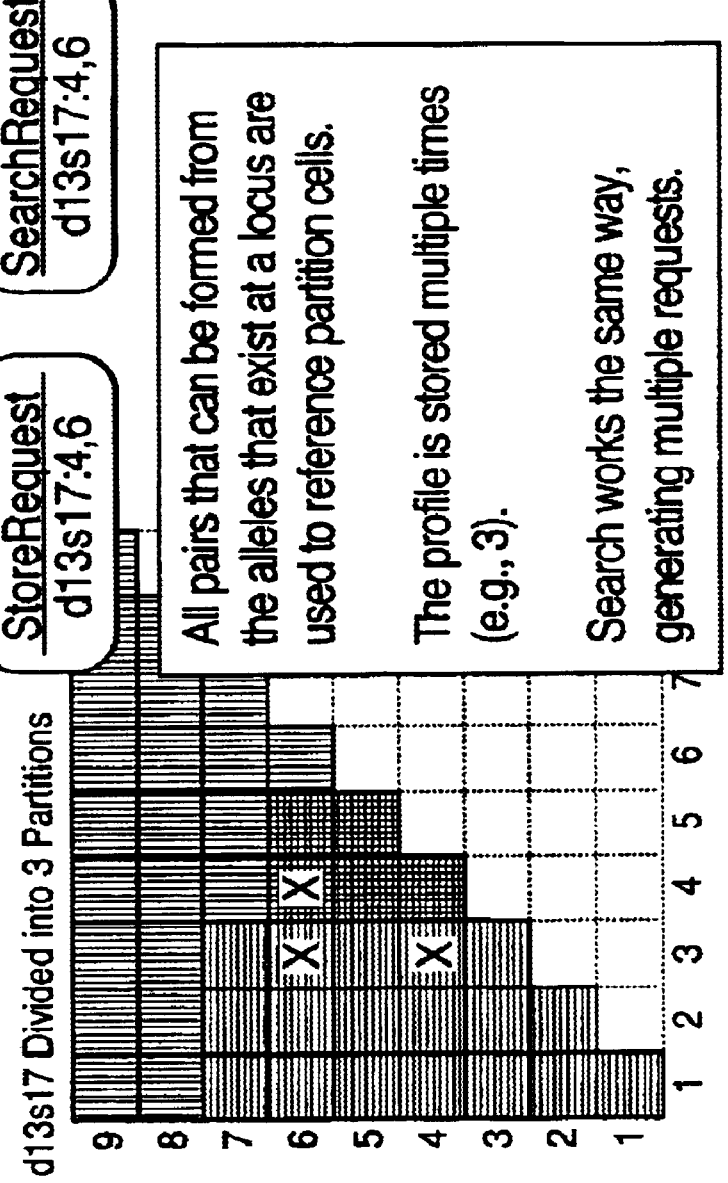
FIG. 11 demonstrates search requests at loci with more than two alleles.

DNA profile loci can contain more than two alleles due to the presence of mixed samples (DNA material from multiple individuals). In this case all pairs that can be formed from the alleles that exist at a locus are used to reference partition cells. In FIG. 11 the DNA profile target contains the alleles 3, 4, and 6 at the d13s17 locus. As a result, the allele pairs (3,4), (3,6), and (4,6) are used to determine new Search Requests.

CODIS defines the concept of match stringency. High stringency matches require the presence of exactly the same alleles at the locus in the target and retrieved samples. Medium stringency allows additional alleles to be present in the retrieved samples and some loci, and low stringency allows a partial correspondence between the alleles to trigger a match. Work on implementation of the medium and low stringency match methods is in progress; however, conceptually these cases are very similar to what is required for equivalent alleles and RFLP error bounds.

In order to discuss how thresholds on the maximum number of allowed misses and the minimum number of required matches are handled, it is necessary to describe a representation of Search Request objects. Misses due to the absence of information for a locus can be handled in a similar fashion. These thresholds affect the number of Node objects in the tree that must be evaluated and can lower search performance if they are chosen poorly. A Search Request object can maintain the following information:

node: the node number in the database tree where the search is to occur (initially zero, indicating the root node)

pPartPrfl: a pointer to the search information (partition profile)

pResult: a pointer to a place to put search results mismatch: a count-down counter of mismatches allowed. The mismatch counter is an example of the Search Request object's ability to carry search state information. This counter specifies the number of misses that may be accumulated from the current point on in the search. Every time a miss is allowed at a node the mismatch counter is decremented and stored in the new Search Request object.

A missing allele is equivalent to the homozygous case. Missing locus data can be handled using either of two approaches. The first uses a special partition entry to reference profiles with no information for the locus. The second stores profiles with missing alleles in all partition entries of the partition corresponding to the locus which would be capable of matching the profile if an allele were present. The first method increases the size of the database tree; the second method increases the number of nodes that must be searched. Because the second method essentially removes the ability to avoid searching partitions having no entries, the first method is preferred.

A constraint can be placed on the maximum number of matching DNA profiles. Search Queue objects can provide the Search Engines with an indication that the maximum number of targets has been returned for a specific search request, causing the Search Engines to ignore subsequent search requests with the same identifier. The Search Queue objects receive this notification from the Server Client, which receives matching DNA profiles as they are generated.

The CODIS completeness condition is fairly complex, requiring the determination that specific combinations of loci data are present in matching DNA profiles. This condition is evaluated only at leaf nodes of the database tree to exclude profiles that fail the requirement.

EXAMPLE 5

Multivariate Statistical Clustering Method

This section provides a description of a method that uses multivariate statistical methods to determine clusters that can be utilized to partition portions of a database into groups of roughly equal size. As a result, this method generates partition information that can be incorporated within or associated with an arbitrary Node object in a database tree. The application of this method to DNA profile data based upon amplification of short tandem repeat (STR) DNA locus data is presented. For this case, a clear binary encoding of the alleles present at a STR locus is available. For other data types, such as DNA RFLP allele (band) data, the proper choice of a binary encoding scheme is not as easy to determine, and at the present time the binary encoding is necessary.

The DNA STR profiles in the database are first represented in a binary form, using a '1' to denote the presence, and a '0' to denote the absence of an allele at a locus. Based on the allele distribution patterns among two chosen STR loci, clusterable patterns are discernable after principal component analysis of the data matrix. Distinct clusters, usually less than 10, can be established using a clustering method, such as k-means [12]. The membership of each cluster is then identified and recorded. Each DNA STR profile belongs to one and only one of these clusters. Thus, the entire set of DNA profiles in the data base can be partitioned into these clusters, based on the allele distribution at these two chosen loci.

When searching for matching profiles to a target profile, the target's DNA profile can be classified into one of these clusters, based on its allele distribution information at these two loci. Thus, a subsequent search can be restricted to members within this cluster. This reduces the search problem by approximately one order of magnitude.

The search process continues by examination of the target's allele distribution at other pairs of STR loci, resulting in classification to a subsequent PCA cluster and reduction of the number of possible matches by another order of magnitude at each level of the database tree. Partitions based on PCA clustering can be inserted into a nonterminal Node object of the database tree at any point and freely intermixed with partitions based upon entropy/adjacency partition assignment.

EXAMPLE 6

Binary Representation of the STR Profile

The STR profiles are first converted into a binary format, with a '1' representing the presence and a '0' the absence of an allele at each locus. Thus the binary representation of a collection of DNA STR profiles is a sparse matrix of mostly zeros and some ones. Each row of this matrix is the representation of one DNA STR profile. The maximum number of 1's for each profile (for samples that are not mixtures of material from two or more individuals) is two times the number of loci, assuming heterozygous presence of alleles at each locus. The minimum number of '1's is equal to the number of loci used for each profile, assuming homozygosity at all loci.

EXAMPLE 7

Clustering by Principal Component Analysis

Principal component analysis (PCA), a popular method of performing multivariate statistical analysis, represents a matrix of high dimension, consisting of correlated information, with a much lower dimensional matrix, without sacrificing significant information contained in the original data matrix. PCA involves a rotation from the original frame of reference to a new frame of reference, whose axes are given by the principal components from the PCA. The first principal component represents the direction along which the variance exhibited by the original data points is maximized. The second principal component, orthogonal to the first, represents the direction along which the remaining variance is maximized. Additional principal components are defined in a similar fashion.

EXAMPLE 8

PCA by Singular Value Decomposition

Figure 12:
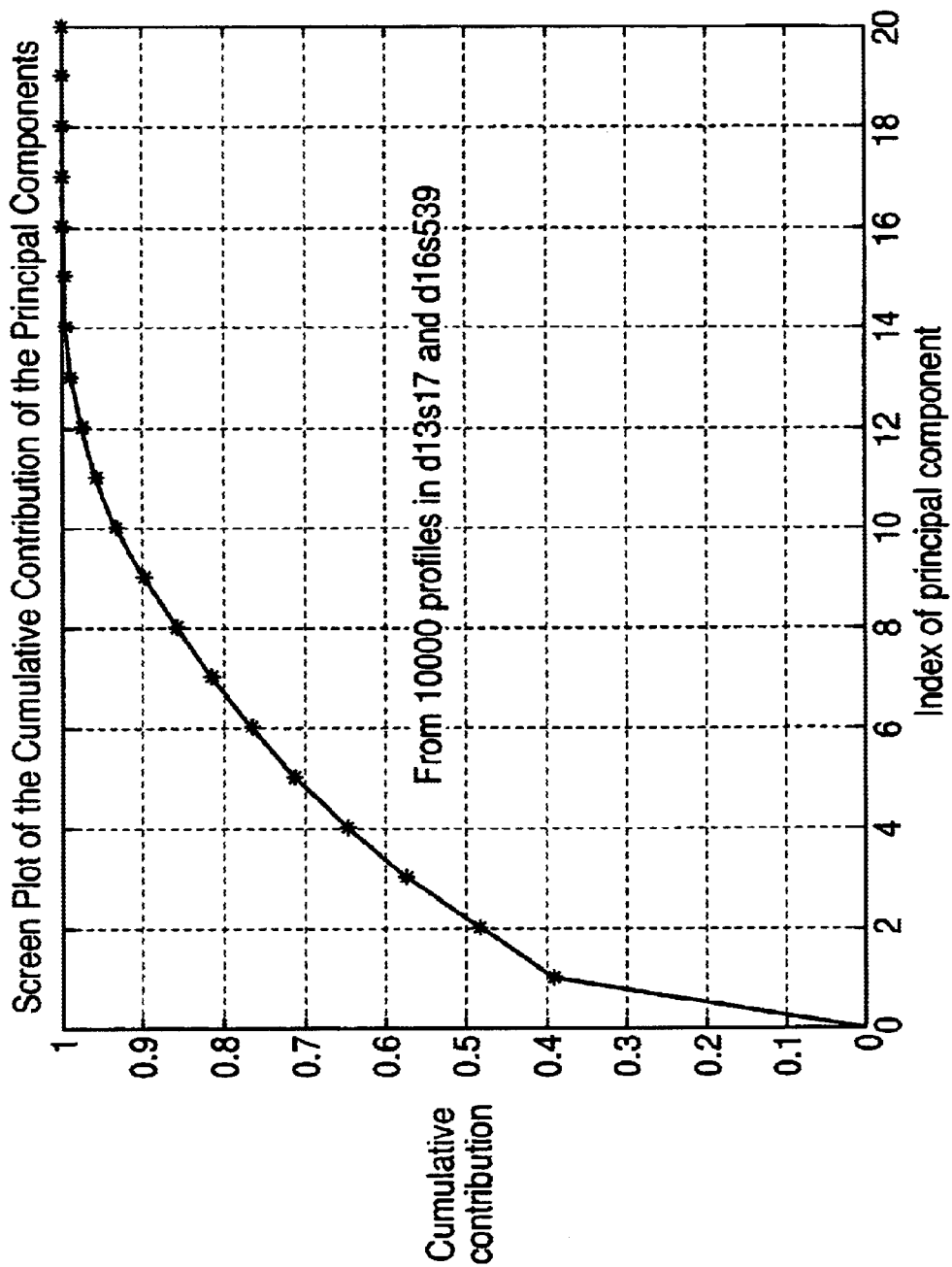
FIG. 12 presents a Scree plot showing the cumulative contribution made by each principal component.

To implement PCA, the preferred method is to use the singular value decomposition (SVD) [9] to decompose the data matrix, X, into the product of three matrices, in which the columns of the matrix, V, are referred to as the "principal components" of the PCA of the data matrix, X. Other methods known in the art may be used to obtain equivalent information. Thus, $$X = U\Sigma V^T \quad (\text{Eq. 1})$$

where U and V are orthogonal matrices, and Σ is a diagonal matrix with positive elements arranged in descending order. The columns of V, being the principal components, represent the coordinates or basis of the axes of the new frame of reference. The ratio of the square of each singular value to the total sum of squares of all the singular values represents the percentage of the total variation contributed by each principal component. A Scree plot can be developed to show the cumulative ratio of this measure; an example is shown in FIG. 12. Since the original data are assumed to be heavily correlated, and the singular values are arranged in descending order, one can make a decision as to how many principal components to keep in building the PCA model to represent the original data. The discarded data along the remaining principal components are regarded as less important and are ignored.

EXAMPLE 9

The Principal Components

Each principal component is of unit length and orthogonal to all other principal components. The principal components are the columns of the right singular matrix, V, of the SVD of the data matrix, X, above. Each principal component is expressed as a linear combination of the original variables, with the entries of the principal component expressing that particular linear combination. The absolute values of all entries are less than or at most equal to 1. Therefore, those entries with relatively large values indicate the heavier weight their corresponding original variables occupy in making up this particular principal component. The variables with correspondingly heavy weights are also the ones being correlated in the original data set. If the columns of the data matrix X are not first mean centered, such that the mean of each treated column is zero, then the first principal component reflects the average values of the variables represented in the new principal component frame of reference. It is then the next few principal components that serve to differentiate between profiles. Therefore, mean centering is an optional step which provides no additional capability and is not performed here.

EXAMPLE 10

The Scores Vectors and Normalized Scores Vectors

After the principal components are found, each data profile can be projected onto each principal component. The projected vector is referred to as the scores vector. The length of the scores vector indicates how closely aligned that data profile is to that principal component. The bigger the projection, the better this principal component represents this data profile. Thus, data profiles with comparable projections onto this principal component can be regarded as "similar" to each other, with respect to this principal component. Those profiles with high projected values onto this principal component indicate that these profiles are highly aligned with that of the principal component, therefore representing more of the original variables which are heavily weighted in that principal component. Similarly, projections of data profiles onto each of the succeeding principal components can be carried out to get the scores and their projections onto those principal components.

Figure 13:
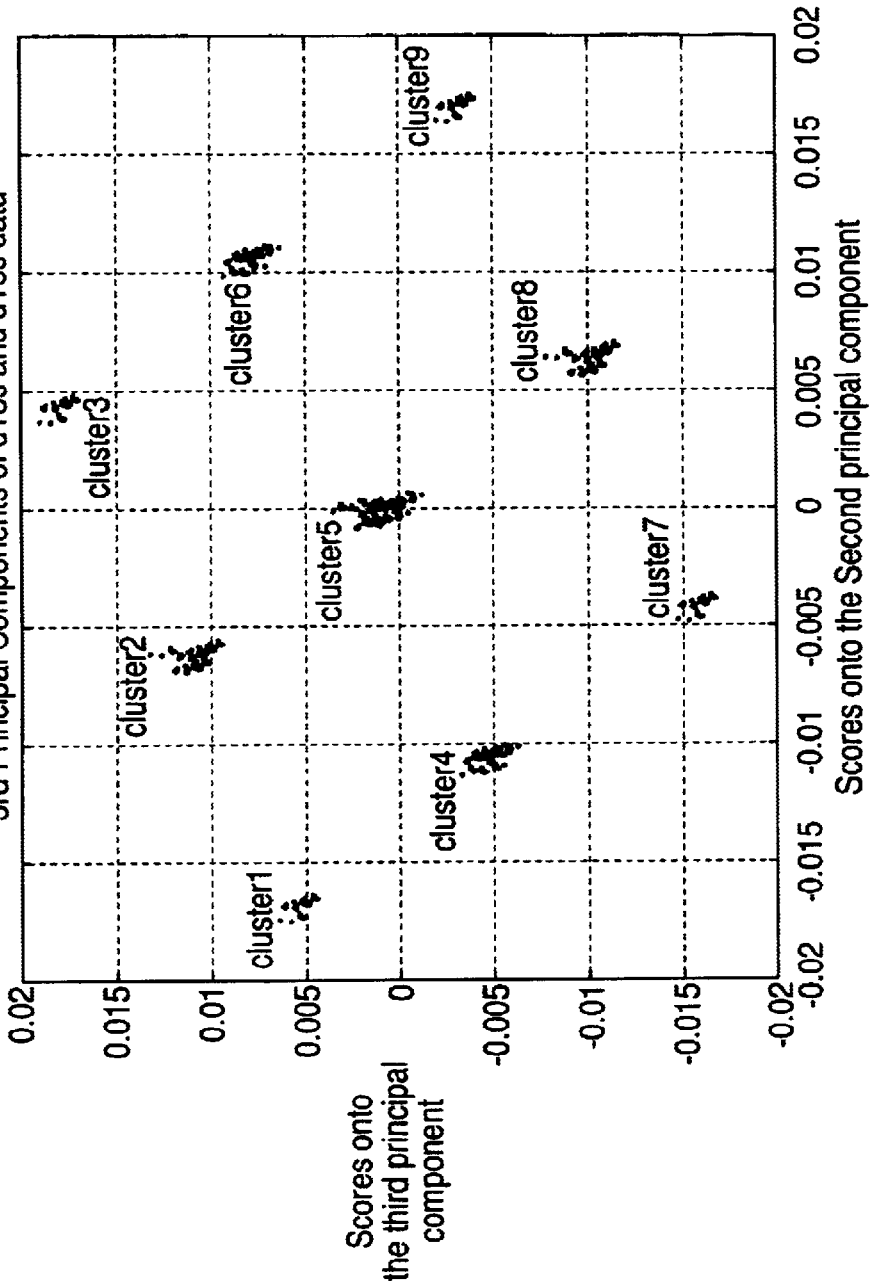
FIG. 13 shows Mahalanobis scores onto principal components 2 and 3 of the 10000 data profiles with alleles in d13s17 and d16s539.

Because of the different degree of variation exhibited by the data profiles along the different principal components, normalization is necessary, such that normalized distances from the origin to each projected point can be compared meaningfully to each other. Therefore, the Mahalanobis distance measure [12] is employed, in which each projection is divided by the corresponding singular value. The Mahalanobis distance scores are calculated as follows:

$$\text{Mahalanobis\_scores} = XV\Sigma^{-1} = (U\Sigma V)V\Sigma^{-1} = U \quad (\text{Eq. 2})$$

where X represents the original data matrix, and U, Σ and V are from the SVD of X, as shown in Eq. 1. Postmultiplying X by V performs the projection of the rows of X (profiles) onto the principal components, with the projected vectors represented with respect to the principal component axes. Postmultiplying XV by $\Sigma^{-1}$ scales each column of XV by the corresponding singular values contained in Σ. A two dimensional plot can be used to show the scores onto principal components PC2 and PC3. In plotting the scores plot in, say PC2 and PC3, it is the row entries from the second and the third columns of the Mahalanobis_scores matrix (the U matrix in Eq. 2) that are plotted in a 2-d plot. From henceforth, the Mahalanobis_scores shall simply be referred to as the scores. An example of such plot is shown in FIG. 13, which shows the scores for 10000 DNA STR profiles in the ds13s17 and d16s539 loci onto the 2nd and 3rd principal components. It is in such a scores plot that clusterability of the sample points is examined.

EXAMPLE 11

Identification of Clusters

A clustering algorithm can be employed to perform clustering of the scores projected onto a 2-d principal component space. K-means [12] is selected because of its wide use and simplicity. However, with k-means the number of clusters has to be specified before the algorithm can begin. This is not a problem because the choice of the two loci, the two principal components on which to project the data, as well as the number of clusters associated with the scores, are all identified by a priori visual inspection and recorded.

K-means clustering starts with an arbitrary set of n points, where n denotes the number of desired clusters, to serve as the center of each cluster. Each data point is assigned to that cluster to which it is "closest" using a distance measure of the user's choice. The standard Euclidian distance measure is used here. This is followed by a calculation for the new center points of the resultant n clusters. Then, in the next round of iteration, clusters are re-formed by assigning to each of the new centers points that are now closest to each. Iterations continue the cluster centers no longer change or a specified number of iterations is reached.

After clusters are formed, the membership of each cluster can be identified and the corresponding DNA STR profiles can be extracted from the original database for future study.

EXAMPLE 12

Projection of New DNA STR Data Set onto the Principal Components of Another

The DNA STR profiles of one group can be compared to that of another by comparing the corresponding scores patterns onto a principal component reference frame. To do the comparison, the projections of the profiles of the second set may be normalized by the inverse of the singular values of the first set. The projection and the normalization to arrive at the Mahalanobis scores of the second data set is carried out as follows:

$$M\_scores_{2nd} = X_{2nd} V_{1st} \Sigma_{1st}^{-1} \quad (Eq. 3)$$

M_scores denotes the Mahalanobis scores, which shall simply be referred to as the scores. In plotting the scores plot in, say PC2 and PC3, it is the row entries from the second and the third columns of the M_scores matrix that are plotted in a 2-d plot.

EXAMPLE 13

Principal Component Analysis of the Synthetic Data in 2 Loci

Study of clustering by PCA was carried out with two sets of data. The first was a synthetic data set, generated from the known allele frequency distribution for each of sixteen STR loci. The distribution is from the CODIS data base. A binary set composed of 10,000 profiles with allele specifications at 16 loci was thus generated. This data matrix has the dimension of 10,000 by 202, and is sparse with all entries either 1 or 0. Each row denotes the STR profile in all 16 loci for one individual; each element of a column represents the presence (1) or absence (0) of the corresponding allele in the each of the 10,000 individuals. The second set of data studied was compiled from human population studies and released by B. Budowle [10] of the FBI, and is composed of DNA STR information of six ethnic groups with about two hundred samples in each group. A PCA model was developed with the large synthetic data set, and the small real data set was projected onto the principal components derived from the former. Relative percentages of membership profiles in the clusters were also compared between the large and the small data sets in order to compare the corresponding allele frequency distributions.

The locus pair of d13s17 and d16s539 was chosen for illustration of the PCA analysis and clustering study. The columns corresponding to the alleles of these two loci from the 10,000 by 202 synthetic data set were extracted, and subjected to singular value decomposition (SVD) to obtain the principal components (the columns of the V matrix in Eq. 1) and the Mahalanobis scores vectors (the columns of the U matrix in Eq. 1). The corresponding columns of the data matrix, X, extracted are columns 11 through 19 (corresponding to alleles 7–15 of the d13s17 locus) and columns 20 to 30 (corresponding to alleles 5–15 of the d16s539 locus) for a total of 20 columns. The SVD of this submatrix of size 10,000 by 20 was computed. First, the number of principal components to retain to build the PCA model was ascertained. FIG. 12 is the Scree plot showing the cumulative contribution made by the principal components. The plot shows that the first three principal components together capture about 60% of the total variation exhibited by the original data matrix. It further shows that the rank of the matrix is 14, meaning there are only 14 independent columns among the total of 20 columns of X. Note that each successive principal component contributes less to the overall data variation, as foreshadowed by the decreasing magnitude of each successive singular value squared of the data matrix, X.

EXAMPLE 14

Scores Plot onto PC2 and PC3

The 10,000 profiles with alleles at d13s17 and d16s539 were projected onto the second and third principal components, followed by normalization by the inverse of the corresponding singular values to arrive at the Mahalanobis scores. The entries of each row after projection and normalization were plotted in a 2-d scores plot. FIG. 13 shows the result. Nine distinct clusters were observed.

EXAMPLE 15

Analyzing the Clusterability of Other 2-Loci Combinations

The clusterability of other 2-loci combinations was also studied. There are a total of 16 loci available for analysis. Therefore, a total of 120 2-loci combinations (16*15/2=120) were analyzed. Table 2 shows those 2-loci combinations and the corresponding supporting principal components that yield good and distinct clusters. The reason that only certain 2 loci combinations yield good clusters is further analyzed so as to understand the role the alleles at each locus play in determining the clusterability of the profiles. The following subsections present the rationale. Briefly, however, those loci pairs with allele probability densities concentrating at just a few of alleles tend to yield good and distinct clusters.

TABLE 2

Combinations of two loci that give good clusters. The corresponding principal components are shown, as well as the number of clusters. V1 and V2 denote the identity of the first and the second principal component specification, onto which good clustering of the projected scores is observed.

| Locus 1 | Locus 2 | V1 | V2 | N clusters |
| --- | --- | --- | --- | --- |
| csf1po | fga | 2 | 3 | 7 |
| csf1po | tpox | 2 | 3 | 7 |
| d13s17 | d16s539 | 2 | 3 | 9 |
| d13s17 | d1s80 | 2 | 3 | 9 |
| d13s17 | d21s11 | 2 | 3 | 9 |
| d13s17 | d5s818 | 2 | 3 | 9 |
| d13s17 | d7s820 | 2 | 3 | 9 |
| d13s17 | fga | 3 | 4 | 7 |
| d13s17 | ho1 | 2 | 3 | 9 |
| d13s17 | vwa | 2 | 3 | 9 |
| d16s539 | d1s80 | 2 | 3 | 9 |
| d16s539 | d5s818 | 2 | 3 | 9 |
| d16s539 | d7s820 | 2 | 3 | 9 |
| d16s539 | fga | 4 | 5 | 7 |
| d16s539 | tho 1 | 2 | 3 | 9 |
| d16s539 | vwa | 2 | 3 | 9 |
| d18s51 | d1s80 | 4 | 5 | 7 |
| d18s51 | d21s11 | 2 | 3 | 7 |
| d18s51 | d3s1358 | 2 | 3 | 7 |
| d18s51 | d5s818 | 2 | 3 | 7 |
| d18s51 | d8s1179 | 2 | 4 | 7 |
| d18s51 | fga | 2 | 3 | 7 |
| d18s51 | tpox | 4 | 5 | 7 |
| d18s51 | vwa | 2 | 3 | 7 |
| d1s80 | fga | 3 | 4 | 7 |

TABLE 2-continued

Combinations of two loci that give good clusters. The
corresponding principal components are shown, as well as
the number of clusters. V1 and V2 denote the identity of
the first and the second principal component specification, onto
which good clustering of the projected scores is observed.

| Locus 1 | Locus 2 | V1 | V2 | N clusters |
|---------|---------|----|----|------------|
| d21s11  | d5s818  | 2  | 3  | 9 |
| d21s11  | d7s820  | 2  | 3  | 9 |
| d21s11  | fga     | 2  | 5  | 9 |
| d21s11  | tho 1   | 2  | 3  | 9 |
| d21s11  | vwa     | 2  | 3  | 9 |
| d3s1358 | fga     | 2  | 3  | 7 |
| d3s1358 | tpox    | 2  | 3  | 7 |
| d5s818  | d7s820  | 2  | 3  | 9 |
| d5s818  | tho 1   | 2  | 3  | 9 |
| d5s818  | vwa     | 3  | 4  | 7 |
| d7s820  | d1s80   | 2  | 3  | 9 |
| d7s820  | d8s1179 | 2  | 3  | 9 |
| d7s820  | vwa     | 2  | 4  | 7 |
| d8s1179 | fga     | 3  | 4  | 7 |
| vwa     | fga     | 2  | 3  | 7 |

EXAMPLE 16

Cluster Formation

Figure 14:
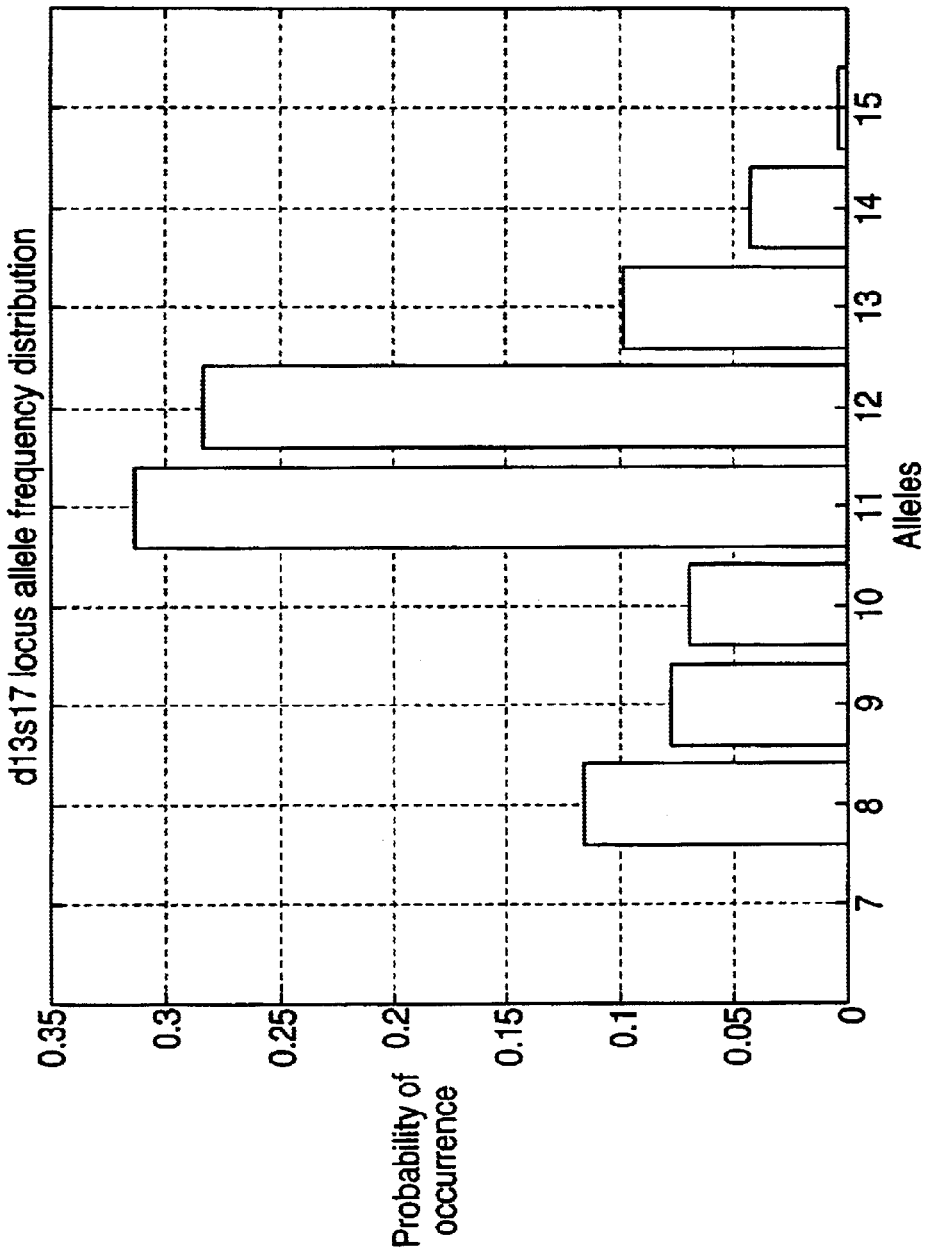
FIG. 14 shows the allele frequency distribution for the d13s17 locus.
Figure 15:
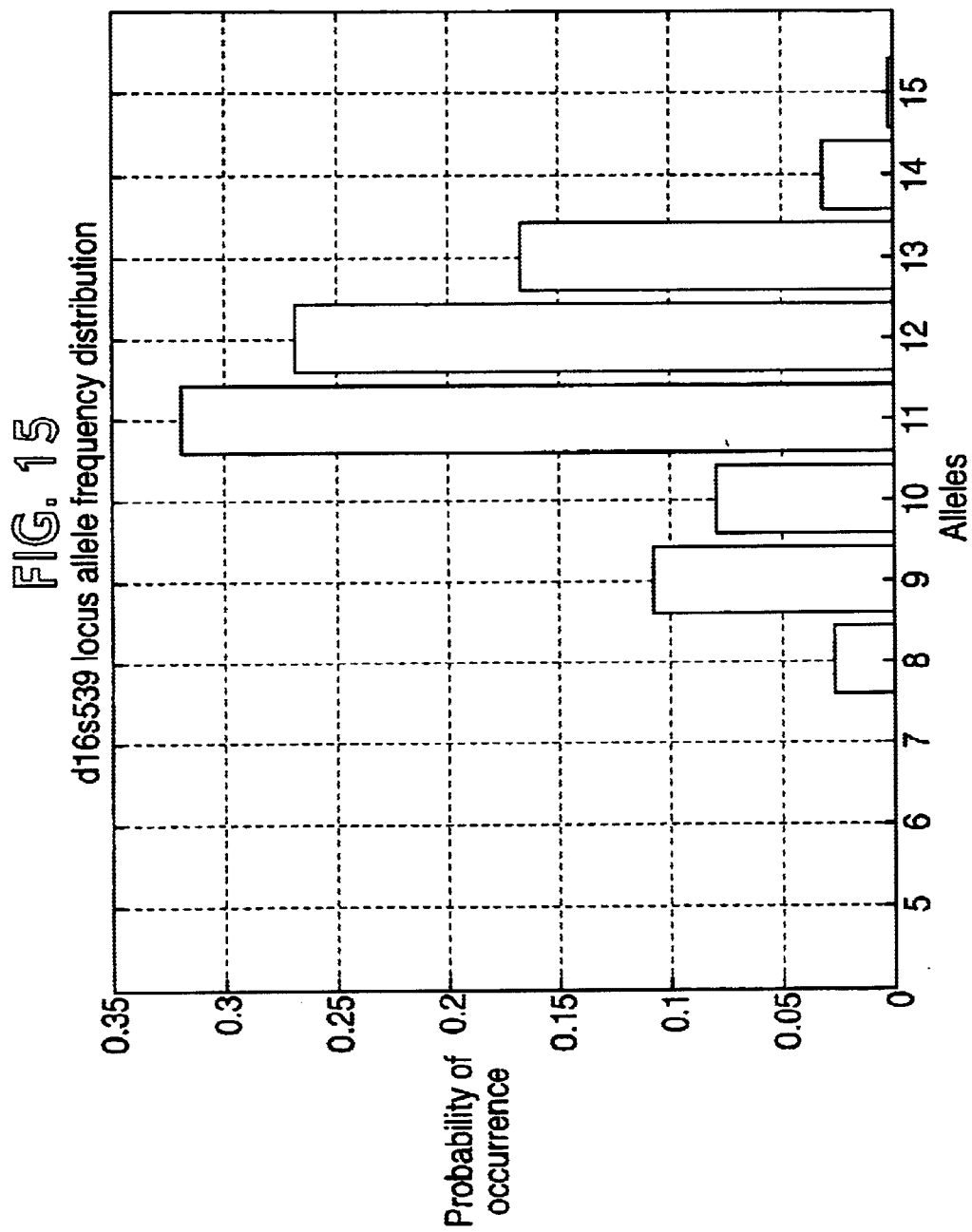
FIG. 15 shows the allele frequency distribution for the d16s539 locus.
Figure 16:
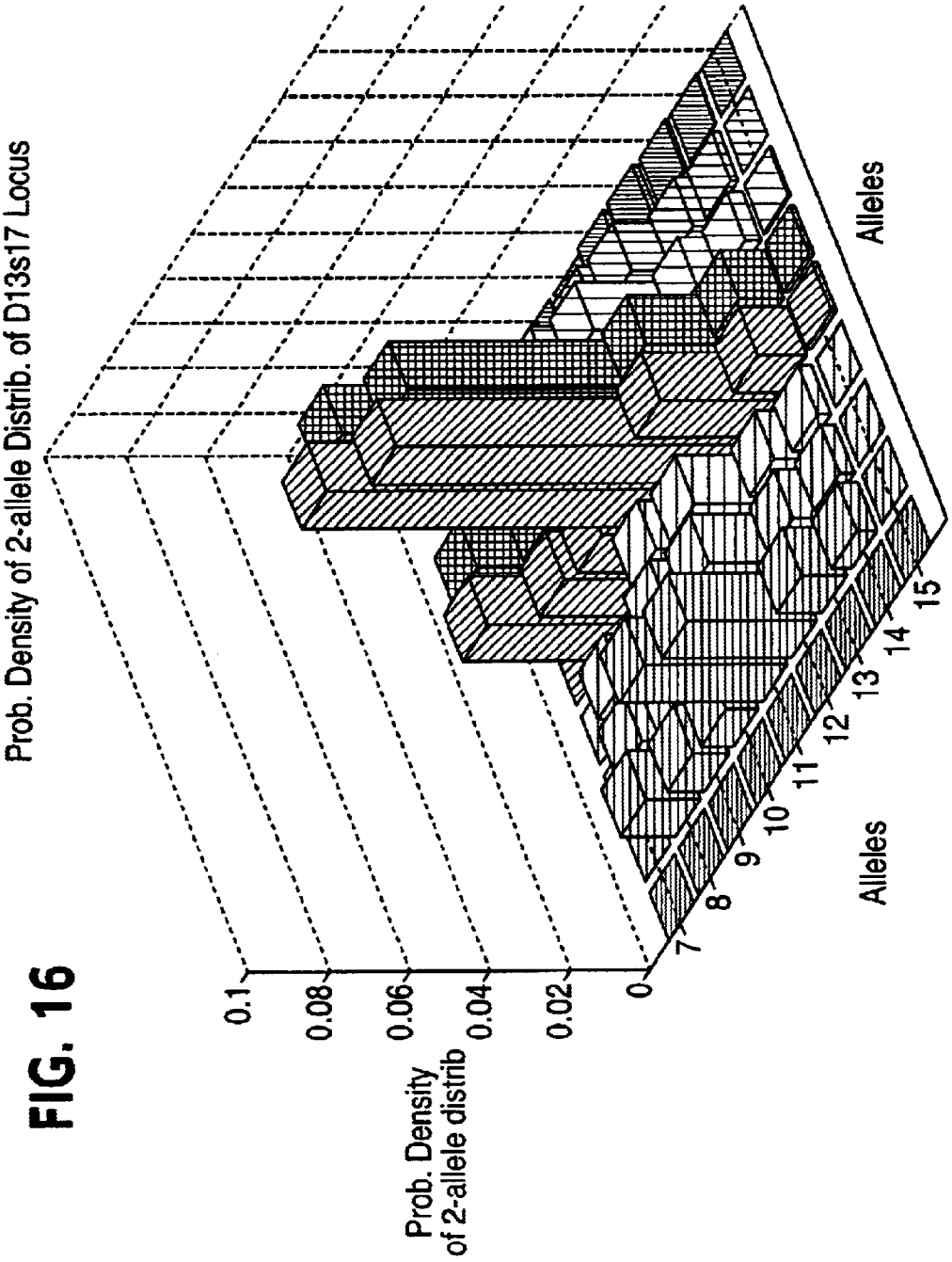
FIG. 16 shows the joint probability density of 2-allele distribution in the d13s17 locus.
Figure 17:
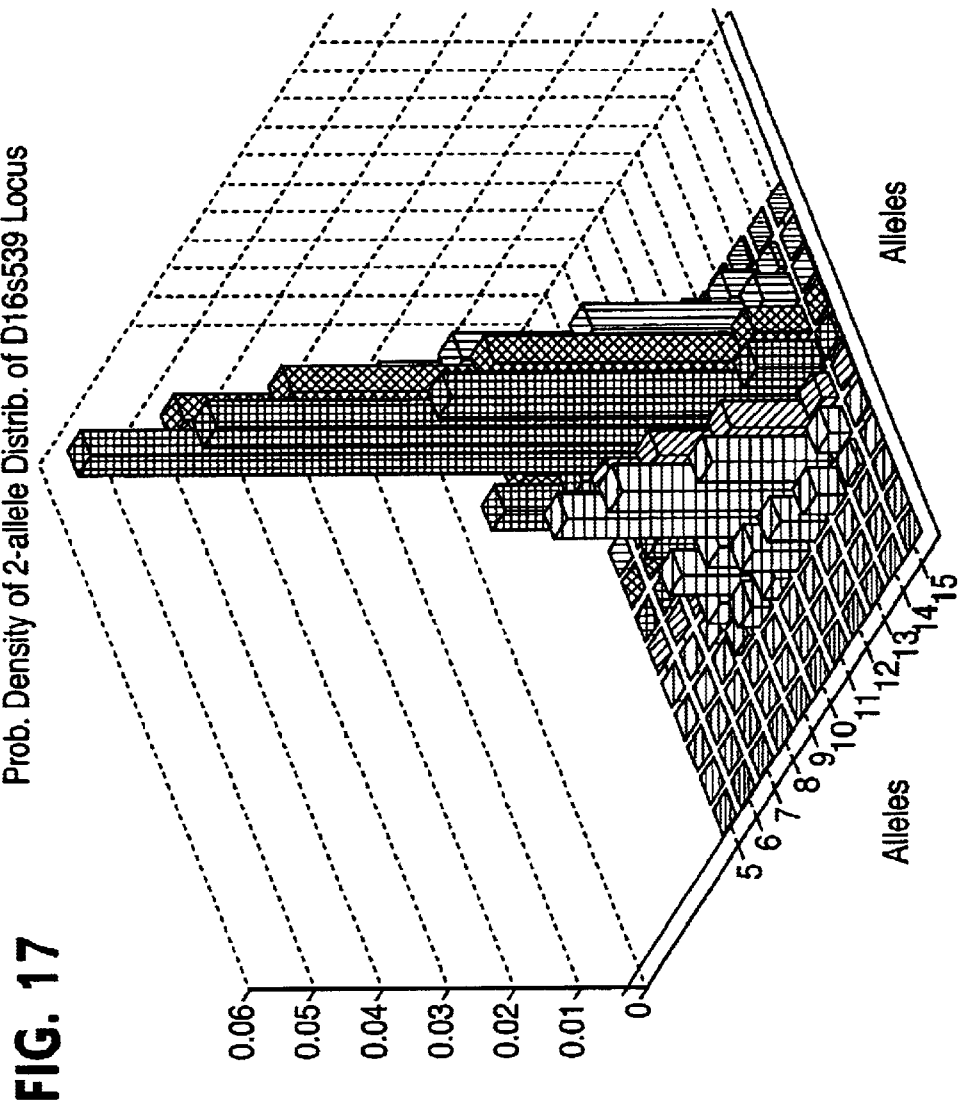
FIG. 17 shows the joint probability density of 2-allele distribution in the d16s539 locus.
Figure 18:
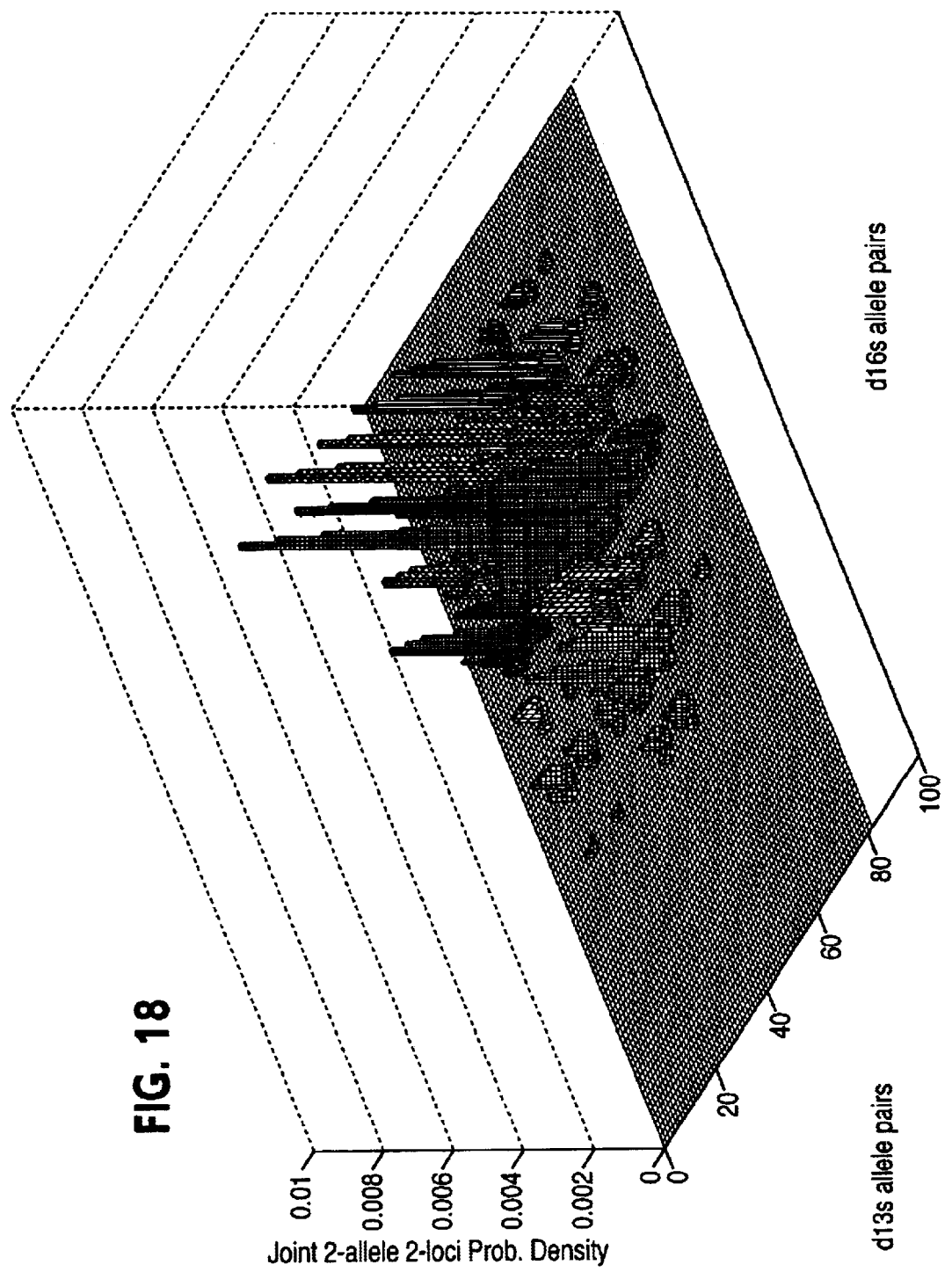
FIG. 18 shows a joint 2-loci allele pair probability distribution pattern.

The allele frequency distributions for the 2-loci combinations that yielded good clusters were examined to discover the reason behind their clusterability. It was found that those loci with allele probability concentrated at just a few alleles (2 to 4) are good candidates to give good clusters. The main reason is that with just a few alleles possible, the joint 2-loci allele distribution tends to concentrate in those allele pairs with relatively high probability of occurrence. Thus less but more distinct clusters tend to be formed. FIGS. 14 and 15 show the relative frequency of occurrence of the alleles at the d13s17 and d16s539 locus, respectively. Notice that alleles 11 and 12 in both loci have a much higher probability of occurrence. FIGS. 16 and 17 show the joint 2-allele frequency distribution for the d13s17 and d16s539 locus respectively. It is noted that only a few of the allele pairs have relatively high probability of occurring. This distribution pattern is to be contrasted with one where the majority of the allele have some probability of occurring but none is much higher than others. FIG. 18 shows the joint 2-loci allele-pair probability density for the d13s16 and d16s539 loci. Again, it is observed that most probability densities are concentrated at a few selected allele pairs, corresponding to those alleles with relatively high probability of occurring within each locus.

EXAMPLE 17

Interpreting SVD of Data Exhibiting Good Clusterability

Consider the allele distribution patterns in a large DNA STR data set. If for a specific locus, the probability densities concentrate in only a few, for example 3 out of 10, alleles, then the majority of the profiles in this data set will have alleles for that locus, corresponding to those with high probability densities. However, some, though in the minority, will still have alleles with low probability densities. Thus, the variance among the profiles associated with this locus will be higher than those where a large number of alleles have comparable but low probability densities. The large variance exhibited by this part of the data will be picked up by the leading principal components of the original data matrix. Recall that the principal components of a matrix X are given by the right singular vectors of X, after SVD (the columns of the matrix, V, from Eq. 1). For a matrix without any column mean centering, the first principal component generally gives just the average of the overall data, and therefore is not useful in differentiating between the points. The second principal component, therefore, is the one that gives the direction along which the variance exhibited by the original data matrix is maximum; the third principal component gives the direction that captures the next maximum variance, after the component along the first and second principal component have been subtracted off from the original data matrix.

As a result of the above reasoning, the first few leading principal components after the first, should be contributed heavily by those original variables (i.e., the alleles) that have the concentrated allele probability densities. FIGS. 19 and 20 show the make up of the second and the third principal components of the 10,000 profiles at the d13s17 and the d16s539 loci.

EXAMPLE 18

Interpreting the Principal Components

It is clear from the FIGS. 19 and 20 that the most significant alleles in principal component 2 are alleles 11 and 12 of d13s17, and the most significant for principal component 3 are alleles 11 and 12 of d16s539. Alleles 11 and 12 of d16s539 also contribute some to PC2, and alleles 11 and 12 of d13s17 also contribute some to PC3. Notice the opposite signs of alleles 11 and 12 of each locus in each PC. What this means is that, if a cluster of the scores of the DNA profiles projects highly onto the positive direction of PC2, then most members within this cluster have the presence of allele 12 (the second tall bar of FIG. 19) of d13s17, the presence of allele 11 of d16s539 (the first tall bar of d16s539 of FIG. 19), the absence of allele 11 in the first locus, and the absence of allele 12 in the second locus, respectively, since the signs associated with the latter pair are negative.

It was observed that cluster 9 from the scores plot of FIG. 13 projects highly along the positive direction of PC2. In FIG. 21 it is evident that in cluster 9, "all" of the members have allele 12 of the d13s17 locus, as well as allele 11 of the d16s539 locus. Further, none of the profiles has allele 11 of the first and allele 12 of the second locus. With similar reasoning, it is observed that cluster 7 projects heavily along the negative direction of the third principal component. This is interpreted to be that the members in this cluster would have allele 11 of both loci, and the absence of allele 12 in both loci. In fact, 100% of the members are this way. Notice that cluster 5 projects almost to the dead center of the origin. This is interpreted to be that members in this cluster either have both alleles or neither allele for each locus, so that the effects of the elements of the principal components for each locus cancel. As seen in FIG. 21, this is the case.

EXAMPLE 19

Clustering by k-Means and Differentiation of Clusters

The nine distinct clusters can be established analytically by the k-means cluster algorithm. Clusters identified by k-means were validated by visual inspection. Memberships within each cluster were analyzed to get at the similarity among the members. FIG. 21 shows a plot of the fraction within each cluster possessing each allele. It is observed that clusters differ in the combination of alleles at each of the 2 loci that are dominant (allele 11 and 12 of both loci). For instance, members of cluster 1 all have the 5th allele of the d13s17 locus (allele 11) and the 8th allele(17−9=8; d13s17 has 9 alleles) of the d16s539 locus (allele 12). From the make up of the principal components, the projections of each clusters onto each principal component can be predicted by looking at the presence or absence of these alleles in the members of the clusters.

Because the most probable alleles for the d13s locus are alleles 11 and 12, and the most probable alleles for d16s539 are alleles 11 and 12 (or index number 16 and 17 in FIG. 21 below), the clusters correspond to profiles with various combinations of presence or absence of these dominant alleles at these four positions. Table 3 shows the combinations of these four dominant alleles in each of the nine clusters, based on the plots shown in FIG. 21. The assignment of the allele distribution in these four dominant alleles in each of these nine clusters as well as the factor that caused the points to cluster this way is further elaborated below.

From Table 3, Boolean expressions can be written that form logical tests on the data to determine cluster assignment. For example, a Boolean expression testing for membership of a DNA profile in cluster 1 is "(d13s17-allele11) and not (d13s17-allele12) and not (d13s539-allele11) and (d13s17-allele12)", where the terms in parentheses are logical variables that are true if the corresponding allele is present and false otherwise. A more complex example is the Boolean expression testing for membership in cluster 5: "(((d13s17-allele11) and (d13s17-allele12)) or not ((d13s17-allele11) or (d13s17-allele12))) and (((d16s539-allele11) and (d16s539-allele12)) or not ((d16s539-allele11) or (d16s539-allele12)))". This expression requires both alleles from each locus to be either present or absent in order to be true. Boolean expressions can be rewritten in various forms and simplified according to methods that are well known and practiced in the fields of Boolean algebra and logic circuit design.

Table 3 can also be utilized to form a decision tree that sequentially applies tests for the presence or absence of alleles at specific loci using the methods of inductive inference that were pioneered by J. Ross Quinlan [13] and are well known and practiced in the fields of computer science and engineering. In this case, each node of the database tree that utilizes clusters derived from the multivariate statistical analysis method would contain a decision tree specifying the sequence of tests to be applied to DNA profile targets at that node, and the database tree can be rewritten by expanding these nodes and incorporating the decision tree's nodes into the database tree.

TABLE 3

The presence (1) or absence (0) of alleles 11 and 12 in the d13s and d16s loci for each scores cluster as shown in FIG. 13.

| Cluster | D13s17 allele 11 | D13s17 allele 12 | D16s539 allele 11 | D16s539 allele 12 |
|---|---|---|---|---|
| 1 | Yes (1) | No (0) | No (0) | Yes (1) |
| 2 | Yes (1) | Yes (1) | No (0) | Yes (1) |
| 2 | No (0) | No (0) | No (0) | Yes (1) |
| 3 | No (0) | Yes (1) | No (0) | Yes (1) |
| 4 | Yes (1) | No (0) | No (0) | No (0) |
| 4 | Yes (1) | No (0) | Yes (1) | Yes (1) |
| 5 | Yes (1) | Yes (1) | Yes (1) | Yes (1) |
| 5 | Yes (1) | Yes (1) | No (0) | No (0) |
| 5 | No (0) | No (0) | Yes (1) | Yes (1) |
| 5 | No (0) | No (0) | No (0) | No (0) |
| 6 | No (0) | Yes (1) | No (0) | No (0) |
| 6 | No (0) | Yes (1) | Yes (1) | Yes (1) |
| 7 | Yes (1) | No (0) | Yes (1) | No (0) |
| 8 | No (0) | No (6) | Yes (1) | No (0) |
| 8 | Yes (1) | Yes (1) | Yes (1) | No (0) |
| 9 | No (0) | Yes (1) | Yes (1) | No (0) |

EXAMPLE 20

What Makes the Points Cluster

The consequence of having the allele probability densities concentrated in just a few alleles of a locus is now analyzed. As presented previously, the SVD of a matrix decomposes a data set into its mutually orthogonal components arranged in decreasing order of the amount of variance carried. Each scores vector is obtained by multiplying each DNA profile (a row of the data matrix, X) by the columns of the V matrix of Eq. 1 above. The columns of V are the principal component vectors. The ith element of a scores vector represents the inner product of that profile with the ith column of V. Table 4 shows the make up of the V2 and V3 vectors (the second and third principal components). Note that the 5th and 6th (allele 11 and 12 of d13s17) as well as the 16th and 17th (allele 11 and 12 of d16s539) components in each vector are dominant (but have opposite signs with each other) with the highest absolute values among all the elements. The significance of this was explained in the previous sections.

During the projection step, the inner product of a row of the DNA profile matrix with each of these V column vectors is formed to produce the scores vector associated with that DNA profile. Recall that a row of the DNA profile consists of 1's and 0's, with a 1 indicating the presence of that allele whose position the 1 occupies. Therefore, in forming the inner product, if a 1 is present at the 6th and 16th positions (corresponding to allele 12 of the d13s locus and allele 11 of the d16s locus) and a 0 is present at the 5th and the 17th positions (corresponding to the absence of allele 11 and allele 12 of d13s and d16s respectively), then the resultant inner product is going to be the highest in the positive sense, of all possible allele presence/absence pattern. The other elements of the V vector are insignificant because their magnitudes are significantly smaller than these four dominant ones. In contrast, if the opposite is true in that the patterns of 1's and 0's are reversed in these four alleles, then a score with the highest value in the negative sense will result. If a 1 is present in only one of the four dominant alleles then an intermediate number will be formed upon taking the inner product. The inner product with V2 gives the projection onto the 2nd principal component, and thus the x-axis coordinate in the 2-d scores plot. The inner product with V3 gives the projection onto the 3rd principal component, and thus the y-axis coordinate in the same plot. Therefore, all profiles with a similar distribution of 1's and 0's among these four dominant allele positions will be projected close to each other, forming a cluster. Profiles with 1's present in only one of the four dominant alleles will be projected into separate and distinct groups intermediate between the two extreme clusters. Profiles with 0's present at all four of these dominant allele positions will project into a cluster close to the origin.

The non-dominant components of V2 and V3 contribute "noise" that causes diversity among the points in each cluster. Cluster assignment is determined by the dominant components. These dominant components correspond to specific alleles whose presence or absence determine cluster membership. A manual or automated procedure can be utilized to determine which loci pairs will exhibit good clusters. The preferred pairs of loci are those that have few dominant components in V2 and V3. A second discovery is that the PCA method tends to produce clusters of roughly equal size. This is a consequence of the relative magnitudes of the probability densities over the alleles at each locus and the grouping of patterns of the alleles that correspond to the dominant components. The PCA method tends to produce groupings of allele patterns that result in clusters of roughly equal size. This property is important because it leads to the generation of balanced database trees, and thus tends to minimize average and worst-case search times.

TABLE 4

The second (V2) and third (V3) principal components of the PCA model for d13s17 and d16s539 profiles.

| Entry | Locus | Allele | V2 | V3 |
|---|---|---|---|---|
| 1 | d13s17 | 7 | 0 | 0 |
| 2 | d13s17 | 8 | −0.030463678 | 0.015674884 |
| 3 | d13s17 | 9 | 0.014273974 | −0.02612085 |
| 4 | d13s17 | 10 | 0.002730887 | 0.006265153 |
| 5 | d13s17 | 11 | −0.60159885 | −0.31240033 |
| 6 | d13s17 | 12 | 0.61424995 | 0.40528092 |
| 7 | d13s17 | 13 | 0.01506822 | −0.027059415 |
| 8 | d13s17 | 14 | 0.008189252 | −0.002920761 |
| 9 | d13s17 | 15 | 0.00040002 | 0.00072532 |
| 10 | d16s539 | 5 | −3.96254E-16 | 1.24058E-16 |
| 11 | d16s539 | 6 | −1.21109E-16 | 3.920160E-17 |
| 12 | d16s539 | 7 | 3.16893E-16 | −1.01547E-16 |
| 13 | d16s539 | 8 | 0.00016862 | −0.005327745 |
| 14 | d16s539 | 9 | −0.009021359 | 0.035054583 |
| 15 | d16s539 | 10 | 0.010145883 | 0.009643393 |
| 16 | d16s539 | 11 | 0.36385758 | −0.61572765 |
| 17 | d16s539 | 12 | −0.3559744 | 0.59259863 |
| 18 | d16s539 | 13 | −0.006374183 | 0.068562668 |
| 19 | d16s539 | 14 | 0.002505632 | 0.009997444 |
| 20 | d16s539 | 15 | −0.000962222 | 0.000468172 |
| | | Scaling facor | 0.015208802 | 0.015862441 |

The center of each cluster is the center of gravity of the swarm of points in that cluster. Table 5 shows where the centers are with respect to the 2-d scores plot of FIG. 13. Based on the above rationale for formation of the clusters, the approximate centers of the nine clusters as observed in the scores plot of FIG. 13 can be predicted from the set of all possible 1's and 0's distribution among the four dominant allele positions. The prediction can be checked against the true centers of the clusters. This is explained in the following section.

TABLE 5

The coordinates of the centers of the nine clusters shown in FIG. 13.

| Cluster Centers | |
|---|---|
| x | y |
| −0.0168 | 0.0054 |
| −0.0062 | 0.0116 |
| 0.0045 | 0.0179 |

TABLE 5-continued

The coordinates of the centers of the nine clusters shown in FIG. 13.

| Cluster Centers | |
|---|---|
| x | y |
| −0.0105 | −0.0052 |
| 0.0001 | 0.0011 |
| 0.0108 | 0.0074 |
| −0.0042 | −0.0159 |
| 0.0064 | −0.0096 |
| 0.0171 | −0.0033 |

EXAMPLE 21

Testing the Theory of Clustering by Predicting the Approximate Centers of the Clusters Table 6 shows all the possible 1-0 distribution patterns at the four dominant allele positions. The approximate predicted x and y coordinates for the cluster centers are calculated by multiplying the corresponding 1's and 0's at the four dominant allele positions with their counterpart values in the V1 (to get the x coordinate) and V2 (to get the y coordinate) vectors which were shown in Table 3 previously. This is followed by a normalization step in which the previous products are multiplied by the scaling factors shown at the bottom of Table 5, in order to arrive at the Mahalanobis scores. These scaling factors correspond to the reciprocals of the 2nd and 3rd singular values of the SVD of the original data matrix, X. The predicted approximate coordinates for the cluster centers are shown at the rightmost two columns of Table 5. These points are plotted as the 'o' points in FIG. 22. The true cluster centers are also plotted in FIG. 22, as the '*' points. It is evident that the two sets are very close. All profiles in the original 10,000 profile set with identical allele distribution pattern in these four dominant allele positions will map to the same cluster. They will differ from each other somewhat, due to the presence or absence of alleles at other allele positions, which play a minor role in determining the coordinates of the corresponding profile in the 2-d scores plot. All possible allele distribution patterns in the four dominant positions fall into a total of nine clusters, as shown in Table 3 above. This experiment supports the explanation rendered above in regard to the formation of clusters in the 2-d scores space.

In summary, loci with allele probability densities concentrating at just a few alleles will give rise to V vectors with preferentially big values (in the absolute value sense) at just a few positions corresponding to the allele positions with high densities. (The fact that both alleles 11 and 12 in the d13s and d16s loci are the dominant alleles are just a coincidence.) As a result, distinct clusters will form, separable by the presence or absence of alleles at these dominant allele positions.

TABLE 6

The presence (1) or absence (0) of alleles at the four dominant allele positions and the approximate cluster center coordinates calculated from the 1-0 allele distribution pattern. See text for calculation of these approximate coordinates.

| | d13s17 | | d16s539 | | Projections | |
|---|---|---|---|---|---|---|
| N | 11 | 12 | 11 | 12 | x | y |
| 1 | 0 | 0 | 0 | 0 | 0 | 0 |
| 2 | 0 | 1 | 0 | 0 | 0.009342 | 0.006429 |
| 3 | 1 | 0 | 0 | 0 | −0.00915 | −0.00496 |
| 4 | 1 | 1 | 0 | 0 | 0.000192 | 0.001473 |
| 5 | 0 | 0 | 0 | 1 | −0.00541 | 0.0094 |
| 6 | 0 | 1 | 0 | 1 | 0.003928 | 0.015829 |
| 7 | 1 | 0 | 0 | 1 | −0.01456 | 0.004445 |
| 8 | 1 | 1 | 0 | 1 | −0.00522 | 0.010873 |
| 9 | 0 | 0 | 1 | 0 | 0.005534 | −0.00977 |
| 10 | 0 | 1 | 1 | 0 | 0.014876 | −0.00334 |
| 11 | 1 | 0 | 1 | 0 | −0.00362 | −0.01472 |
| 12 | 1 | 1 | 1 | 0 | 0.005726 | −0.00829 |
| 13 | 0 | 0 | 1 | 1 | 0.00012 | −0.00037 |
| 14 | 0 | 1 | 1 | 1 | 0.009462 | 0.006062 |
| 15 | 1 | 0 | 1 | 1 | −0.00903 | −0.00532 |
| 16 | 1 | 1 | 1 | 1 | 0.000312 | 0.001106 |
| | Scaling factor: | | | | 0.0152088 | 0.0158626 |

EXAMPLE 22

Clustering Analysis of a Real DNA STR Data Set

All the work reported above was done with 10,000 synthetic data profiles, generated based on the allele frequency distribution data for Caucasians as given in the CODIS data base. Recently, Budowle [10] released the STR profiles of six ethnic groups, each of which has around 200 samples. We tested whether PCA clusters from these data would project to the same clusters as that of the synthetic data, using the principal components from the latter to do the projection, and if the relative sizes of the clusters were maintained. Therefore, a small Caucasian sample data set from one of the six real DNA sample set was chosen for further analysis. This was done to determine whether or not new data inserted in the database would tend to degrade the balanced structure of the database tree and thus adversely affect mean and worst case search times.

The sample set was first converted to the binary representation format, with 1's and 0's. The corresponding allele information in the d13s17 and d16s539 loci was extracted. This was followed by computing the scores matrix onto the 2nd and 3rd principal components of the large synthetic data set. FIGS. 23 and 24 show the results. In FIG. 23, the scores points from the large data set are overlaid on top of the scores points from the small data set. FIG. 24 shows the same thing except in this plot, the scores from the small sample set are overlaid on top of those of the large sample set. The black points depict the scores from the small sample set. Since there are only 176 of them, they do not completely cover the 10000 score points from the large data set. It is evident that the plotted scores from the small data (which are mapped to the same 2-d coordinates in a cluster as the scores from the large data set and are plotted as darker dots) are completely covered by those of the large data set (the dark gray points). This was interpreted to mean that there is no profile present in the small real DNA sample set that is not present in the large synthetic data set. This complete coverage is not always the case. Studies using other 2-loci combinations sometimes yield incomplete coverage. In all instances studied to date, however, the plotted 2-d coordinates for points in the small datasets were easily associated with clusters identified using the synthetic data set.

Next, estimates of the probability densities associated with the various clusters are derived. We identified which profiles from the small sample data set are in each of the nine clusters. We then calculated the fraction of the sample population that are within each of the nine clusters. FIG. 25 shows the comparison between the two data sets. The first bar of each pair of bars represents that from the small sample set, while the second bar denotes that of the large data set. To a first level approximation, the relative fractions are comparable between the two sets. The fraction of people in each cluster indicates the approximate fraction of people possessing the particular combination of the alleles at the dominant allele positions, thus the relative frequency of the occurrence of those dominant alleles in the associated locus. Note that the trend of the variation of the height of the bars for both sets are similar, except for that of the last cluster. It was concluded at this point that the two data sets have similar allele frequency distribution at these two loci. An important observation is the relative frequencies indicate that the sizes of the clusters are balanced in both data sets. This implies that addition of the data from Budowle to a database containing the synthetic data will not cause a database tree that utilizes clustering for the (d13s17, d16s539) locus pair to be unbalanced. Thus, search times will not be adversely affected.

EXAMPLE 23

Summary for the Clusterability of Profiles by the Principal Component Analysis Approach This method can be extended by either (a) using more than two loci or (b) using more than two principal components (or both) to form clusters. It is possible, however, to utilize too much information, in which case clustering will not be achieved. For example, the use of PCA methods to analyze allele information for 16 loci simultaneously does not exhibit clustering. Thus, an important discovery of the inventors is that it is advantageous to limit the application of PCA methods to a portion of the available information to achieve good clustering results. In the work illustrated here, the information was limited to allele data for two loci. In this case, 40 out of 120 possible two-loci combinations exhibited good clustering properties, as listed in Table 3.

It is firmly established that DNA STR profiles can be partitioned into distinct clusters using the PCA approach. The partition is based on the allele distribution pattern at 2 loci. Certain 2-loci choices yield much better clustering than others. The factors that determine good clustering and the reason for the clustering have been presented and discussed. Successive partitioning using a different 2-loci combination approach at each round will reduce very quickly the members present within each resultant cluster. Partitioning by PCA clustering can be inserted into a suitably chosen non-terminal Node object of the database tree structure, for searching for matching profiles against a target profile. After passing through this node, it is expected that the number of candidate profiles for search will be reduced by approximately one order of magnitude. (Seven to nine clusters usually result from PCA clustering in which the clusters are about equal in size.)

EXAMPLE 24

Performance Analysis

The existing FBI CODIS database search engine requires approximately 5 seconds to search 100,000 DNA profile records for matches. In comparison, a database of synthetic DNA profile data was created using the statistical information provided with the FBI CODIS database. This database contained 400,000 DNA profiles and required a database tree with 13 levels and 13,180 Node objects. The memory required to store the tree was 218 Mbytes. The time required to load the database from an ASCII file that contained descriptions of the DNA profiles was 19 minutes 22 seconds. Search times for the test cases that have been run to date on the 400,000 profile database range from 1,200 microseconds to 4,200 microseconds, an improvement of greater than a factor of 1,000 over the CODIS implementation. These times are for searches for exact matches.

Additional tests were made using a database of 100,000 DNA profiles. For each test a DNA profile was randomly selected from the database and used to construct a search request. Exact matches were required. Over 5,019 runs the mean time required to complete a search and retrieve the matching sample(s) was 2,132.6 microseconds. Of the 5,019 runs, 98.5% of the searches completed in less than 5,000 microseconds. A histogram showing the distribution of times required to perform the search is shown in FIG. 26.

When locus data are missing the search times increase. For a single target DNA profile match times increased from approximately 1,700 microseconds to 4,200 microseconds on a database of 10,000 samples. When matching is allowed on all but a single locus search times increased by approximately an order of magnitude to 17,000 microseconds. Tests were also conducted when equivalent alleles were defined, but are not directly comparable to the base case because a database of 1,000 DNA profiles was used. Searches required approximately 2,300 microseconds.

Figure 27:
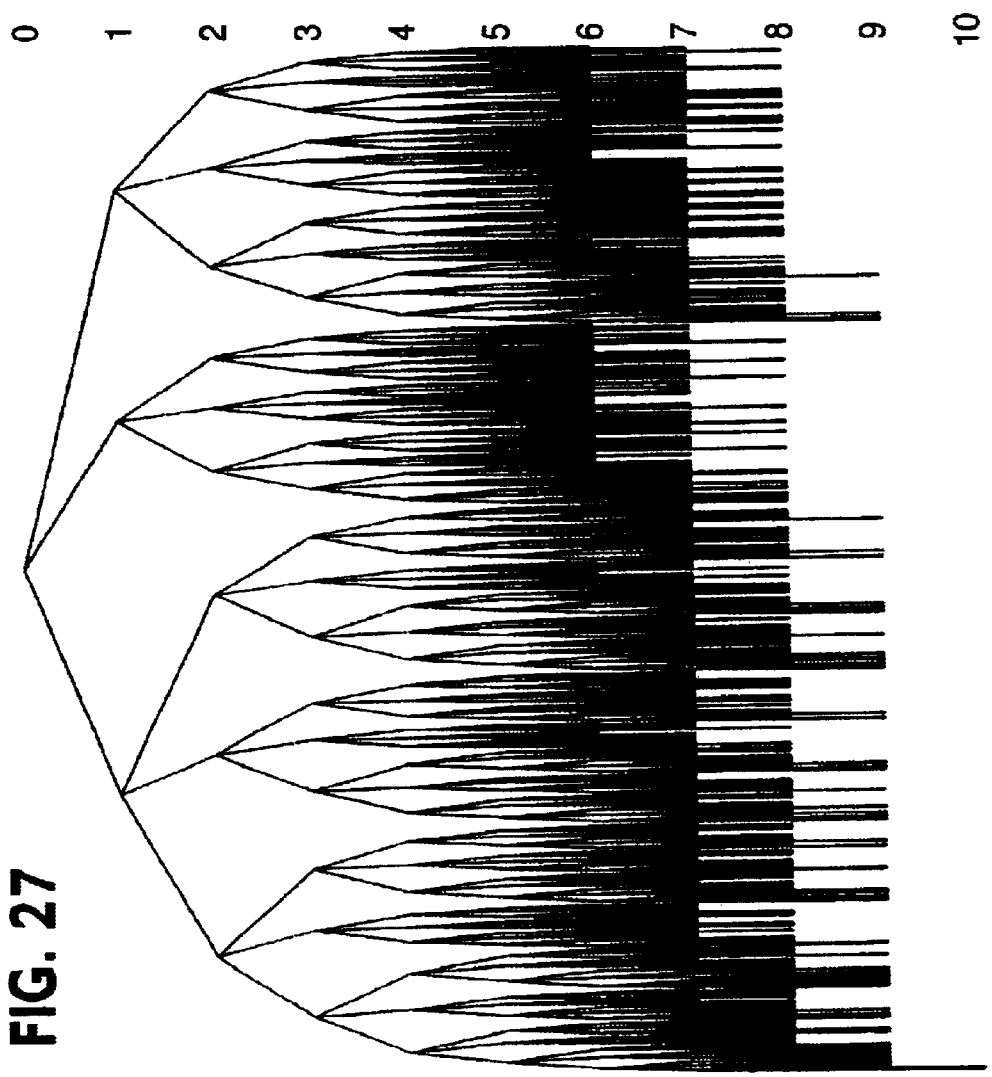
FIG. 27 illustrates a database tree containing 100,000 DNA profiles.

The method of database construction maintains a well-balanced database tree. FIG. 27 shows the graph of the tree for a database holding 100,000 DNA profiles with a maximum of 100 profiles stored at any leaf node. The tree has a maximum depth of 11 (levels 0 through 10) with most branches having a length of 7 to 9. Similar results have been obtained for 400,000 stored DNA profiles where the tree's maximum depth was 13. The balanced characteristic of the tree is important because it determines average and worst case search time. If the tree becomes unbalanced then a substantial fraction of Search Requests will require the descent of relatively long branches and will therefore require additional time.

EXAMPLE 25

Parallel Database Design and Hardware Platform

The database tree methods described above can also be implemented in parallel or by using multi-threaded software. The parallel implementation executes Search Engine and Search Queue objects on each host, with at least as many Search Engine objects as there are processors on a host. A root host is used to accept Client requests and create a Search Client object to handle each request. A critical component of the parallel implementation is the method used to balance the work load across the set of available hosts and processors. This method is distributed; it must run on each host. The method also responds to changing load patterns on the hosts, giving faster hosts more work. The method is reconfigured in the event of host failure(s).

Preferably, each host is allowed to maintain information on the population of available parallel virtual machine (PVM) hosts, measurements of their current loads (Search Queue lengths), and measurements of their capacities. Each host is responsible for gathering its statistics and broadcasting this information to the other participating hosts. As Search Queues become unbalanced, unprocessed Search Requests are exchanged to bring them back into balance. This exchange occurs randomly with a stochastic selection method utilized to determine the recipient of each exchange. In this manner control of the load balancing method equates to control of the probabilities of host selection. These probabilities are preferably proportional to the difference between that host's capacity and its load, weighted by the total of these differences over all hosts. A time constant is utilized to avoid excessive oscillations in host loading.

Two hardware platform options can be employed as hosts for the parallel database implementation. One utilizes generic PC hardware operating under the Linux operating system; the other utilizes a Sun Microsystems HPC 10000 server and the Solaris operating system. Both utilize the Parallel Virtual Machine (PVM) software [7] package to coordinate interprocess communications and synchronization. An asynchronous transfer mode (ATM) interconnect can also be used for the generic PC implementation, utilizing OC-12c (622 Mbps) connections between equipment racks and OC-3c (155 Mbps) connections within each rack. The configuration is scalable from 8 to 128 processors, with two additional control processors, in increments of 16 processors. A Control Rack houses a high performance ATM switch, such as the Fore Systems ASX-1200, configured in a star topology with OC-12c links to the PC Racks. The control rack also houses the control processors, a tape backup subsystem, a video and keyboard switch, and dual uninterruptable power supplies (UPS). A variation of this implementation is to replace the ATM interconnect with Fast Ethernet, Gigabit Ethernet, or another networking approach. Combinations of networking approaches may be used. Performance is dependent on the approach. The approach described is preferred.

The generic PC implementation can contain from one to eight PC racks, each housing eight rack-mounted dual processor PCs, a midrange ATM switch such as the Fore Systems ASX-200, and an UPS. All PC processors are specified as 500 MHz Pentium IIIs, although it is preferable to use the fastest chipset available at the time for construction of the system. Each PC is configured with 512 MB to 1 GB of RAM, and 54 GB of hard disk space. Performance figures of merit for the system include 3.5 TB (terabytes) of disk storage, 64–128 GB aggregate memory, maximum sustained aggregate interprocessor bandwidth of 10 Gbps (non-blocking), with a maximum per PC bandwidth of 155 Mbps and rack-to-rack of 1.24 Gbps (non-blocking in each case). The estimated peak floating point performance on the linpack parallel benchmark is 40–60 Gflops, with an estimated peak aggregate instruction rate of 64 GIPS, assuming 500 MHz processors. This implementation strategy is similar to the Linux Beowulf supercomputer clusters pioneered by NASA [8].

The Sun HPC 10000 server scales from 4 to 64 400 MHz SPARC processors, with a configuration of 4 processors per board and a maximum of 16 boards. Input/output subsystems are attached to each processor board, and a 102 Gbps processor interconnect is utilized with 10 Gbps bandwidth to memory. In excess of 60 TB of disk space can be configured. The HPC 10000 supports clustering with up to 4 HPC 10000's in a cluster. The platform supports both PVM and MPI. Linpack-parallel benchmark results for a 64 processor Sun HPC 10000 have been reported at 43.8 Gflops. Sun claims a peak instruction rate of 100 GIPS.

Each configuration has its merits and disadvantages; however, either configuration can achieve the necessary performance for the national CODIS database. The Sun solution is probably substantially more costly; however, Sun offers maintenance and support contracts. A potential disadvantage of the Sun configuration is the shared memory architecture with a 10 Gbps memory bandwidth limitation. The fully distributed generic PC implementation provides local memory for each processor; however, a disadvantage is setup latency across the ATM switches and contention for the 10 Gbps non-blocking bandwidth of the Fore ASX-1200 switch. A substantial long-term advantage of the generic PC solution is that processors can be readily swapped out at will and upgraded with newer technology. Replacement of failed units with spare rack-mountable computers is also easy, allowing repair as time and resources permit. The generic PC solution has the advantage of being able to track the continuing evolution of processor performance, which has historically provided a rough doubling of performance every 18 months. It is unclear whether similar upgrade paths will be available for the Sun HPC 10000 architecture.

Figure 28:
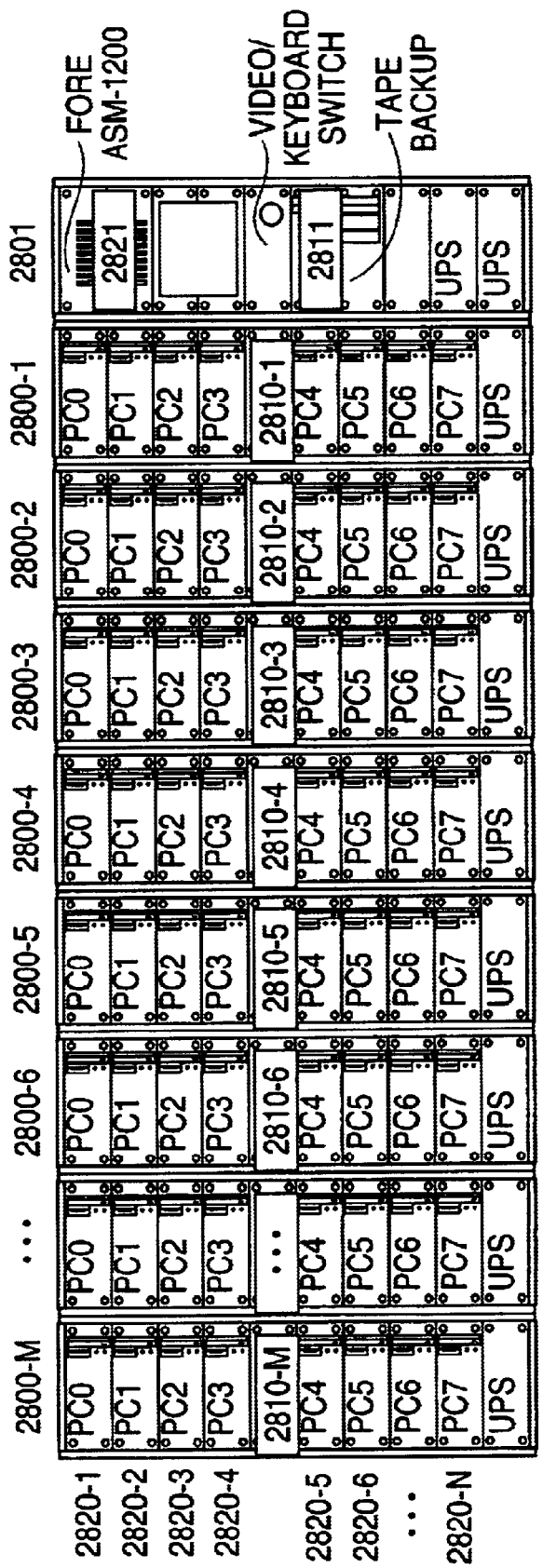
FIG. 28 depicts a parallel architecture implementation of the invention.

Referring to FIG. 28, there is shown an example of a fully developed parallel architecture implementation of the present invention. Panels 2800-1 to 2800-M are fully modular and can grow in increments of one panel to a full complement of M panels (eight of which are shown). Moreover, each panel 2800 comprises two or more processors 2820 such that a first panel may be built and additional panels added in stages as the architecture grows to meet increasing database size and traffic demand of queries and retrievals of the database. Panel 2801 is a control panel and provides control operations for panels 2800-1 to 2800-M using one or more control hosts 2811. Central module 2810-1 to 2810-M of each panel comprises a bus control module providing data linking capabilities and bus control for coupling computer hosts on its panel to bus control module 2821 on control panel 2801 and through bus control module 2821 to control hosts 2811 and all other computer hosts 2820 of panels 2800-1 to 2800-M. Each panel 2800-1 to 2800-M comprises N processors 2820-1 to 2820-N.

References

1. Cormen, Thomas H., Charles E. Leiserson, and Ronald L. Rivest, *Introduction to Algorithms*, MIT Press (Cambridge, Mass.)/McGraw-Hill (New York). 1990.
2. Guttman, A., R trees: a dynamic index structure for spatial searching, ACM, 1984, 47-57.
3. Sellis, T., et. al., The R*-tree: a dynamic index for multi-dimensional objects, Tech. Rept. UMI-ACS TR 87 3, CS TR 1975, University of Maryland, Feb. 1987, 1-24.
4. Agrawal, R. and J. C. Shafer, Method and system for performing proximity joins on high-dimensional data points in parallel, U.S. Pat. No. 5,884,320, Mar. 16, 1999.
5. Message Passing Interface Forum, MPI: A Message-Passing Interface Standard, version 1.1, June, 1995. Also at http://www-unix.mcs.anl.gov/mpi/.
6. Universal Data Option for Informix Dynamic Server, version 9.14 for Windows NT and UNIX. Also at http://www.informix.com/informix/techbriefs/udo/udo.pdf.
7. Geist, A., A. Begnelin, J. Dongarra, W. Jiang, R. Manchek, V. Sunderam, PVM: Parallel Virtual Machine: A Users' Guide and Tutorial for Networked Parallel Computing. MIT Press. 1994.
8. Beowulf Project at CESDIR, http://cesdis1.gsfc.nasa.gov/linux/beowulf/, Center of Excellence in Space Data and Information Sciences, NASA Goddard Space Flight Center. 1998.
9. Strang, G., Linear Algebra and its Applications, 2nd ed., Academic Press, New York, 1980.
10. Budowle, Bruce and Tamyra R. Moretti, "Genotype profiles for six population groups at the 13 CODIS short tandem repeat core loci and other PCR based loci," *Forensic Science Communications*, FBI Laboratory Division Publication 99-06, U.S. Department of Justice, Federal Bureau of Investigation. July 1999, V. 1, n. 2.
11. CODIS 5.1 GDIS Searching Specification (Draft), U.S. Department of Justice Federal Bureau of Investigation. Jul. 23, 1998.
12. Tou, Julius T. and Rafael G. Gonzalez, Pattern Recognition Principles, Addison-Wesley, Reading, Mass., 1992.
13. Quinlan, J. R., Induction of decision trees, Machine Learning 1:81–106, 1986.
14. Berry, Michael W., Zlatko Drmac, and Elizabeth R. Jessup, "Matrices, vector spaces, and information retrieval," SIAM Review 41:335–362, 1999.

We claim:

1. A method of organizing the data records of a database into clusters, comprising the steps of:
    (a) representing one or more variables in each data record in a binary form, whereby the value of each bit is assigned based on the value of a variable;
    (b) choosing a set of variables from those represented in all of the data records, whereby principal component analysis of the set of variables yields distinct clusters of the data records;
    (c) applying principal component analysis to the chosen set of variables for a sample of the data records, whereby two or more principal component vectors are identified;
    (d) examining the scores of the chosen set of variables for the sample data records along the two or more vectors;
    (e) selecting those vectors of the two or more vectors for which the examined scores form distinct clusters;
    (f) formulating a test based on the selected vectors; and
    (g) performing the test formulated in step (f) on each data record, whereby the data records are organized into clusters.

2. The method of claim 1, wherein the value of each bit is assigned in step (a) based on whether the value of a variable is within a designated range of values.

3. The method of claim 1, wherein the value of each bit is assigned in step (a) based on whether a designated value of a variable is present.

4. The method of claim 1, wherein steps (c) through (e) are performed on a sample of data records from a different database.

5. The method of claim 1, wherein the test formulated in step (f) comprises:
    projecting the chosen set of variables from a data record onto the selected principal component vectors;
    scaling the projected values;
    calculating a distance from the vector of scaled projected values to a representative sample vector of each cluster; and
    assigning the data record to the clusters associated with the least distance.

6. The method of claim 5, wherein the representative sample vector of each cluster is the cluster center.

7. The method of claim 1, wherein the data comprise DNA profiles.

8. The method of claim 7, wherein the represented variables are alleles at two or more polymorphic loci.

9. The method of claim 8, wherein the value of each bit is assigned in step (a) based on whether a designated allele is present.

10. The method of claim 1, wherein the chosen set of variables and selected principal component vectors yield distinct clusters of approximately equal size.

11. The method of claim 1, wherein each test defines a partition of data of the database according to one of entropy/adjacency partition assignment or data clustering using multivariate statistical analysis.

12. The method of claim 1 wherein the variable in step (a) comprises more than one value, wherein each of the more than one value is represented in binary form.

13. The method of claim 1 wherein the binary form representation of step (a) is provided as a matrix, said matrix comprising a row for each data record and a column for each value of each variable, and wherein the row for each data record contains binary encoded information regarding the presence or absence of the value of each variable in the data record.

14. A method of organizing the data records of a database into clusters, comprising the steps of:
   (a) representing one or more variables in each data record in a binary form, whereby the value of each bit is assigned based on the value of a variable;
   (b) choosing a set of variables from those represented in all of the data records, whereby multivariate statistical analysis of the set of variables yields distinct clusters of the data records;
   (c) applying multivariate statistical analysis to the chosen set of variables of a sample of the data records, whereby two or more vectors are identified;
   (d) examining the vectors of inner products of the chosen set of variables of the sample data records with the identified vectors;
   (e) selecting the identified vectors that cause the vectors of inner products to form clusters;
   (f) formulating a test based on the selected vectors which assigns each data record to a cluster; and
   (g) performing the test formulated in step (f) on each data record, whereby the data records are organized into clusters.

15. The method of claim 14, wherein the value of each bit is assigned in step (a) based on whether the value of a variable is within a designated range of values.

16. The method of claim 14, wherein the value of each bit is assigned in step (a) based on whether a designated value of a variable is present.

17. The method of claim 14, wherein steps (c) through (e) are performed on a sample of data records from a different database.

18. The method of claim 14, wherein the test formulated in step comprises:
   projecting the chosen set of variables from a data record onto the selected vectors;
   scaling the projected values;
   calculating a distance from the vector of scaled projected values to a representative sample vector of each cluster; and
   assigning the data record to the clusters associated with the least distance.

19. The method of claim 18, wherein the representative sample vector of each cluster is the cluster center.

20. The method of claim 14, wherein the data comprise DNA profiles.

21. The method of claim 20, wherein the represented variables are alleles at two or more polymorphic loci.

22. The method of claim 21, wherein the value of each bit is assigned in step (a) based on whether a designated allele is present.

23. The method of claim 14, wherein the chosen set of variables and selected vectors yield distinct clusters of approximately equal size.

24. The method of claim 14 wherein the variable in step (a) comprises more than one value, wherein each of the more than one value is represented in binary form.

25. The method of claim 14 wherein the binary form representation of step (a) is provided as a matrix, said matrix comprising a row for each data record and a column for each value of each variable, and wherein the row for each data record contains binary encoded information regarding the presence or absence of the value of each variable in the data record.

26. A method of organizing data records of a database into clusters, comprising:
   (a) choosing a set of variables to represent data records of a database and a set of principal component vectors with which the set of variables cluster the data records, said step of choosing being performed by:
      (i) selecting one or more variables present in all of the data records;
      (ii) applying principal component analysis to the selected variables of a sample of the data records to obtain principal component vectors;
      (iii) projecting the selected variables of a sample of the data records onto the principal component vectors;
      (iv) determining whether the projections of the selected variables of the sample of data records form clusters;
      (v) repeating steps (i)–(iv) to obtain the set of variables and the set of principal component vectors that form clusters;
   (b) projecting the variables chosen in step (a) for the data records onto the principal component vectors chosen in step (a);
   (c) formulating a test which assigns each data record to a cluster, wherein the test is based on the variables chosen in step (a);
   (d) performing the test on each data record, whereby the data records are organized into clusters.

27. The method of claim 26, wherein the principal component vectors chosen in step (a) contain two vectors.

28. The method of claim 26 wherein the variables selected in step (a) are represented in binary form based on whether the values of the variables are within a designated range of values.

29. The method of claim 26 wherein the variables chosen in step (a) are represented in binary form, and wherein the value of the variable is assigned based on whether a designated value is present.

30. The method of claim 26 wherein steps (a)(ii)–(a)(iv) are performed on data records from a different database.

31. The method of claim 26 wherein the test comprises:
   projecting a first data record onto the principal component vectors chosen in step (a);
   optionally scaling the projected first data record;
   calculating a distance between the projected first data record and at least one representative vector of two or more clusters; and
   assigning the first data record to the clusters associated with the least distance.

32. The method of claim 31 wherein each representative vector is a cluster center.

33. The method of claim 26 wherein the data records comprise DNA profiles.

34. The method of claim 33 wherein the set of variables chosen in step (a) comprise allele values.

35. The method of claim 34 wherein the allele values are represented based on whether a designated allele is present.

36. The method of claim 26 wherein the set of variables and the set of principal component vectors chosen in step (a) yield distinct clusters of approximately equal size.

37. The method of claim 26 wherein the test defines a partition of the data records of the database according to entropy/adjacency partition assignment or data clustering using multivariate statistical analysis.

38. A method of organizing data records of a database into clusters, comprising:
   (a) choosing a set of variables to represent data records of a database and a set of vectors with which the set of variables cluster the data records, said step of choosing being performed by:
      (i) selecting one or more variables present in all of the data records;
      (ii) applying multivariate statistical analysis to the selected variables of a sample of the data records to identify two or more vectors;
      (iii) determining if vectors of inner products of the selected variables of the data records and the two or more identified vectors in (ii) form clusters;
      (iv) repeating steps (i)–(iii) to obtain the set of variables and the two or more identified vectors that form clusters;
   (b) representing the set of variables selected in step (a) in binary form, wherein the value of each bit is assigned based on the value of the variable;
   (c) calculating vectors inner products between the selected variables of the data records and the two or more vectors chosen in step (a);
   (d) formulating a test which assigns each data record to a cluster, wherein the test is based on the variables chosen in step (a);
   (e) performing the test on each data record, whereby the data records are organized into clusters.

39. The method of claim 38 wherein the vectors identified in step (a)(iii) are two in number.

40. The method of claim 38 wherein the set of variables chosen in step (a) is represented in binary form based on whether the value of the variable is within a designated range of values.

41. The method of claim 38 wherein the set of variables is represented in binary form based on whether a designated value of a variable is present.

42. The method of claim 38 wherein steps (a)(ii)–(a)(iii) are performed on data records from a different database.

43. The method of claim 38 wherein the test comprises:
   projecting a first data record onto the vectors chosen in step (a);
   optionally scaling the projected first data record;
   calculating a distance between the projected first data record and at least one representative vector of two or more clusters;
   assigning the first data record to the clusters associated with the least distance.

44. The method of claim 43 wherein each representative vector is a cluster center.

45. The method of claim 38 wherein the data records comprise DNA profiles.

46. The method of claim 45 wherein the set of variables chosen in step (a) comprise allele values.

47. The method of claim 46 wherein each value indicates whether a designated allele is present.

48. The method of claim 38 wherein the set of variables and the set of vectors chosen in step (a) yield distinct clusters of approximately equal size.

49. The method of claim 26 wherein the test defines a partition of the data records of the database according to entropy/adjacency partition assignment or data clustering using multivariate statistical analysis.

* * * * *

UNITED STATES PATENT AND TRADEMARK OFFICE
CERTIFICATE OF CORRECTION

PATENT NO. : 6,741,983 B1
APPLICATION NO. : 09/671304
DATED : May 25, 2004
INVENTOR(S) : John D. Birdwell It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (652) days Delete the phrase "by 652 days" and insert --by 266 days--

Signed and Sealed this

Tenth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,741,983 B1 Page 1 of 1
APPLICATION NO. : 09/671304
DATED : May 25, 2004
INVENTOR(S) : John D. Birdwell et al.

It is certified that error appears in the above-identified patent and that said Letters Patent is hereby corrected as shown below:

At column 21, line 27, please delete "(d13s539-allele11)" and insert therefor --(d16s539-allele11)--.

At column 21, line 28, please delete "(d13s17-allele12)" and insert therefor --(d16s539-allele12)--.

Signed and Sealed this

Thirteenth Day of February, 2007

JON W. DUDAS
*Director of the United States Patent and Trademark Office*

UNITED STATES PATENT AND TRADEMARK OFFICE
CERTIFICATE OF CORRECTION

PATENT NO.      : 6,741,983 B1                                    Page 1 of 2
APPLICATION NO. : 09/671304
DATED           : May 25, 2004
INVENTOR(S)     : John D. Birdwell et al.

It is certified that error appears in the above-identified patent and that said Letters Patent is hereby corrected as shown below:

FIG. 1: "d13s17" should read as --d13s317--.
FIG. 2: Four instances of "d13s17" should read as --d13s317--.
FIG. 9: "d13s17" should read as --d13s317--.
FIG. 11: Three instances of "d13s17" should read as --d13s317--.
FIG. 12: "d13s17" should read as --d13s317--.
FIG. 14: "d13s17" should read as --d13s317--.
FIG. 16: "D13s17" should read as --d13s317--.
FIG. 23: "d13s17" should read as --d13s317--.
FIG. 24: "d13s17" should read as --d13s317--.
FIG. 25: "d13s17" should read as --d13s317--.
Column 3, line 47: "d13s17 locus" should read as --d13s317 locus--.
Column 4, line 5: "d13s17 locus" should read as --d13s317 locus--.
Column 4, line 7: "d13s17 locus" should read as --d13s317 locus--.
Column 4, line 12: "d13s17 locus" should read as --d13s317 locus--.
Column 4, line 20: "d13s17" should read as --d13s317--.
Column 4, line 25: "d13s 17" should read as --d13s317--.
Column 4, line 29: "d13s17" should read as --d13s317--
Column 5, line 65: "d13s17" should read as --d13s317--.
Column 6, TABLE 1, line 8: "d13s17 locus." should read as --d13s317 locus.--.
Column 12, line 40: "d13s17" should read as --d13s317--.
Column 12, line 65: "d13s17" should read as --d13s317--.
Column 16, line 41: "d13s17" should read as --d13s317--.
Column 17, line 51: "d13s17" should read as --d13s317--.
Column 17, line 60: "d13s17" should read as --d13s317--.
Column 18, line 13: "d13s17" should read as --d13s317--.
Column 18, TABLE 2, lines 48-55: Eight instances of "d13s17" under Locus 1 should read as --d13s317--.
Column 19, line 37: "d13s17" should read as --d13s317--.
Column 19, line 40: "d13s17" should read as --d13s317--.
Column 19, line 46: "d13s16" should read as --d13s317--.
Column 20, line 20: "d13s17" should read as --d13s317--.

Signed and Sealed this

Fourteenth Day of December, 2010

David J. Kappos
*Director of the United States Patent and Trademark Office*

CERTIFICATE OF CORRECTION (continued)
U.S. Pat. No. 6,741,983 B1

Column 20, line 28: "d13s17" should read as --d13s317--.
Column 20, line 31: "d13s17" should read as --d13s317--.
Column 20, line 36: "d13s17" should read as --d13s317--.
Column 20, line 45: "d13s17" should read as --d13s317--.
Column 21, line 5: Two instances of "d13s17" should read as --d13s317--.
Column 21, line 25: "("d13s17-allele 11)" should read as --(d13s317-allele 11)--.
Column 21, line 26: "(d13s17-allele 12)" should read as --(d13s317-allele 12)-- and "(d13s539-allele11)" should read as --(d16s539-allele11)--.
Column 21, line 27: "(d13s17-allele 12)"" should read as --(d13s317-allele 12)"--.
Column 21, line 31: ""(((d13s17-allele11)" should read as --"(((d13s317-allele11" and "(d13s17-allele 12)" should read as --(d13s317-allele 12)--.
Column 21, lines 31-32: "((d13s17-allele 11) or (d13s17-allel12)))" should read as --((d13s317-allele 11) or (d13s317-allele12)))--.
Column 21, TABLE 3, line 58: Two instances of "D13s17" should read as --D13s317--.
Column 22, TABLE 3-continued, line 6: Two instances of "D13s17" should read as --D13s317--.
Column 22, line 33: "d13s17" should read as --d13s317--.
Column 23, TABLE 4, line 26: "d13s17" should read as --d13s317--.
Column 23, TABLE 4, lines 28-36: Nine instances of "d13s17" under "Locus" should read as --d13s317--.
Column 25, TABLE 6, line 8: "d13s17" should read as --d13s317--.
Column 25, line 47: "d13s17" should read as --d13s317--.
Column 26, line 25: "d13s17" should read as --d13s317--.